(12) United States Patent
Nakahara et al.

(10) Patent No.: US 9,554,700 B2
(45) Date of Patent: Jan. 31, 2017

(54) OPTICAL COHERENCE TOMOGRAPHIC IMAGING APPARATUS AND METHOD OF CONTROLLING THE SAME

(71) Applicant: CANON KABUSHIKI KAISHA, Tokyo (JP)

(72) Inventors: Yasuhiro Nakahara, Kawasaki (JP); Manabu Wada, Kawasaki (JP); Hiroki Uchida, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 306 days.

(21) Appl. No.: 14/161,560

(22) Filed: Jan. 22, 2014

(65) Prior Publication Data

US 2014/0211157 A1   Jul. 31, 2014

(30) Foreign Application Priority Data

Jan. 31, 2013   (JP) .................................. 2013-017660

(51) Int. Cl.
  *A61B 3/14*   (2006.01)
  *A61B 3/10*   (2006.01)
  *A61B 3/00*   (2006.01)

(52) U.S. Cl.
  CPC .................................... *A61B 3/102* (2013.01)

(58) Field of Classification Search
  USPC ................................................ 351/200–246
  See application file for complete search history.

(56) References Cited

U.S. PATENT DOCUMENTS

| | | | |
|---|---|---|---|
| 9,211,062 B2 * | 12/2015 | Sakagawa | A61B 3/113 |
| 2010/0053553 A1 | 3/2010 | Zinser | |
| 2011/0267581 A1 | 11/2011 | Nakajima et al. | |
| 2013/0278897 A1 * | 10/2013 | Suehira, I | A61B 3/102 351/206 |
| 2014/0063460 A1 * | 3/2014 | Borycki | A61B 3/12 351/208 |
| 2014/0121506 A1 * | 5/2014 | Iwase | G01B 9/02028 600/425 |
| 2014/0204341 A1 * | 7/2014 | Murase | A61B 3/102 351/208 |
| 2014/0211155 A1 * | 7/2014 | Sakagawa | A61B 3/113 351/206 |
| 2015/0366448 A1 * | 12/2015 | Iwase | A61B 3/0025 351/206 |

FOREIGN PATENT DOCUMENTS

| | | | |
|---|---|---|---|
| JP | 2008029467 A | 2/2008 | |
| JP | 2011-115507 A | 6/2011 | |
| JP | 2012-187230 A | 10/2012 | |

\* cited by examiner

*Primary Examiner* — Mohammed Hasan

(74) *Attorney, Agent, or Firm* — Canon USA Inc., IP Division

(57) ABSTRACT

An optical coherence tomographic imaging apparatus includes a movement amount acquisition unit configured to acquire an amount of rotation of a subject's eye based on a plurality of images of the subject's eye acquired at different times, and a control unit configured to control a scanning unit to correct, based on the acquired amount of rotation, a scanning position between a scan and a next scan performed by the scanning unit.

20 Claims, 18 Drawing Sheets

OPTICAL COHERENCE TOMOGRAPHIC IMAGING APPARATUS AND METHOD OF CONTROLLING THE SAME

BACKGROUND OF THE INVENTION

1. Field of the Invention

The present invention relates to an optical coherence tomographic imaging apparatus for capturing a tomographic image of a subject's eye using the interference of light, and relates to a method of controlling the same.

2. Description of the Related Art

Presently, optical coherence tomographic imaging apparatuses based on optical coherence tomography (OCT) using the interference of light of a plurality of wavelengths are known and used to obtain, for example, visceral information through an endoscope or retinal information through an ophthalmic apparatus. The field of application of the optical coherence tomographic imaging apparatuses to a human body is increasingly broadened. The optical coherence tomographic imaging apparatuses applied to the eye are becoming indispensable as ophthalmic instruments for clinics specializing in retina.

Such an optical coherence tomographic imaging apparatus is an apparatus capable of irradiating a sample with measurement light, which is low-coherent light, and measuring light backscattered from the sample, using an interference system. The apparatus irradiates a point on the sample with the measurement light, and thereby can obtain image information of the sample in the depth direction at the point. Further, the apparatus makes measurements while scanning the sample with the measurement light, and thereby can also obtain a tomographic image of the sample. When applied to the fundus, the apparatus scans the fundus of a subject's eye with the measurement light, and thereby can capture a tomographic image of the fundus of the subject's eye at high resolution. Thus, the apparatus is widely used for the ophthalmic diagnosis of retina.

Generally, an optical coherence tomographic imaging apparatus uses a capturing method for repeatedly scanning the fundus to be measured in a horizontal direction or a vertical direction, thereby obtaining a plurality of tomographic images. The apparatus scans the same location on the fundus a plurality of times to acquire a plurality of fundus tomographic images of the same part. Then, the apparatus performs an averaging process on the plurality of fundus tomographic images, and thereby can obtain a single high-quality fundus tomographic image. Further, the apparatus performs scanning a plurality of times while moving the scanning position in a parallel manner, and thereby can also obtain a three-dimensional image of the fundus. If, however, the apparatus performs scanning a plurality of times as described above, it takes a certain time period to complete all the capturing. Thus, the eye may move during the image capturing.

To solve this problem, the Japanese Patent Application Laid-Open No. 2008-29467 discusses an ophthalmic imaging apparatus having a tracking function for sequentially capturing front images of a subject's eye, detecting the movement of the subject's eye using the plurality of obtained front images, and correcting a scanning position according to the detected movement of the subject's eye.

SUMMARY OF THE INVENTION

According to an aspect of the present invention, an optical coherence tomographic imaging apparatus includes an image acquisition unit configured to acquire a plurality of images of a subject's eye at different times, a tomographic image acquisition unit configured to acquire a plurality of tomographic images of the subject's eye based on interference light obtained by causing light reflected from the subject's eye irradiated with measurement light through a scanning unit, to interfere with reference light corresponding to the measurement light, a movement amount acquisition unit configured to acquire at least an amount of rotation of the subject's eye among amounts of movement of the subject's eye based on the plurality of images, and a control unit configured to control the scanning unit to correct, based on the acquired amount of rotation, a scanning position between a scan and a next scan performed by the scanning unit.

Further features of the present invention will become apparent from the following detailed description of exemplary embodiments with reference to the attached drawings.

DESCRIPTION OF THE EMBODIMENTS

Figure 1:
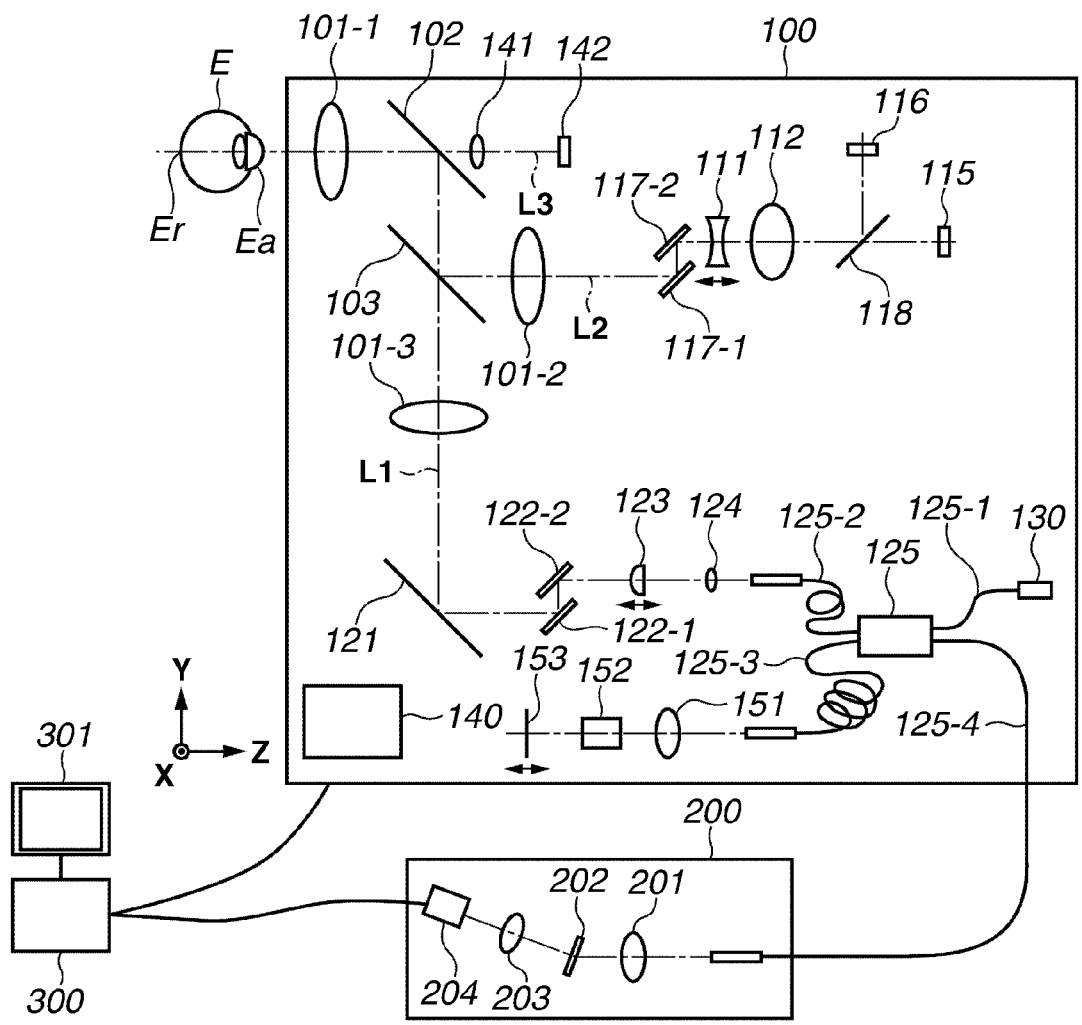
FIG. 1 is a diagram illustrating an example of a configuration of an optical coherence tomographic imaging apparatus according to a first exemplary embodiment.

Generally, there is time lag from the detection of the movement of a subject's eye to the correction of a scanning position. Thus, if a movement in which the amount of movement per unit time is relatively large (a flicking movement among involuntary eye movements during fixation) has occurred among the types of movements of the subject's eye, the following problems arise. First, even if the subject's eye has been tracked according to this movement, distortion occurs in a tomographic image due to the movement itself. Further, distortion occurs also due to the correction of the scanning position shifted by this movement. Similar problems arise in a positional shift due to the rotation of the subject's eye, as well as a positional shift in X and Y directions.

An object of an exemplary embodiment is to acquire a tomographic image as follows. While a subject's eye is being tracked according to the movement of the subject's eye, a movement in which the amount of movement per unit time is relatively large may occur among the types of movements of the subject's eye. Even in such a case, a tomographic image is acquired in which distortion occurring due to this movement is reduced.

An optical coherence tomographic imaging apparatus according to the present exemplary embodiment can acquire, based on a plurality of images (e.g., a plurality of fundus images) of a subject's eye acquired at different times, at least the amount of rotation of the subject's eye among the amounts of movement of the subject's eye. Further, the optical coherence tomographic imaging apparatus according to the present exemplary embodiment can control a scanning unit to correct, based on the acquired amount of rotation, a scanning position between a scan and a next scan performed by the scanning unit.

Further, an optical coherence tomographic imaging apparatus according to another exemplary embodiment can control a scanning unit (control the operation of a unit for tracking a subject's eye) to correct, based on a plurality of images of a subject's eye acquired at different times, a scanning position between a scan and a next scan performed by the scanning unit.

Based on at least one of the exemplary embodiments described above, even if a movement in which the amount of movement per unit time is relatively large has occurred among the types of movements of the subject's eye, it is possible to acquire a tomographic image in which distortion occurring due to this movement is reduced. It is also possible to similarly solve a positional shift due to the rotation of the subject's eye, as well as a positional shift in X and Y directions.

When an operation of fundus tracking has been performed during a capturing of a tomographic image, the correction of the scanning position based on the fundus tracking may cause distortion in the tomographic image. If the correction interval based on the fundus tracking is shorter than the time required for obtaining information of the subject's eye in the depth direction at a point (an A-scan acquisition time), the scanning position is appropriately corrected at each scanning point for obtaining a single tomographic image. Thus, distortion does not occur in the tomographic image. It is, however, difficult to make the correction interval based on the fundus tracking shorter than the A-scan acquisition time. For example, the fundus tracking often uses a front image of the fundus, but it is difficult to make the correction interval based on the fundus tracking equal to or shorter than the acquisition interval of the front image. Generally, the acquisition interval of the front image is about several tens of milliseconds, which is longer than the acquisition interval of the A-scan (generally, several tens of microseconds). Thus, it is difficult to correct the scanning position based on the fundus tracking with respect to each point during the scanning of the subject's eye. Thus, the scanning position is corrected based on the fundus tracking with respect to each certain scanning range at certain intervals. Then, if the scanning position has been corrected at each certain interval, the movement of the eye detected during the certain interval is corrected at a time. This results in causing an abrupt change in the scanning position at each certain interval during the scanning of the subject's eye. Then, the abrupt change in the scanning position appears as a shift (distortion) in the section at each certain interval in the captured tomographic image.

The distortion in the tomographic image as described above may not only hinder diagnostic imaging performed by a doctor, but also cause the doctor to erroneously recognize the distortion in the tomographic image as a lesion. This may lead to a misdiagnosis. Further, the distortion in the tomographic image may have an adverse influence on the function of automatically recognizing the retinal layer boundaries, the function included in many optical coherence tomographic imaging apparatuses. Then, if the retinal layer boundaries have been erroneously recognized, the measured values of the thicknesses of the retinal layers are displayed based on the result of the erroneous recognition. This may lead to a misdiagnosis.

Thus, when a plurality of tomographic images of the subject's eye is acquired, it is desirable to control a tracking unit for tracking the subject's eye. This enables the acquisition of a tomographic image in which distortion occurring due to the movement of the subject's eye is reduced. For example, it is desirable to operate the tracking unit for tracking the subject's eye to, during the period from the acquisition of one of a plurality of tomographic images to the acquisition of a next tomographic image, correct the acquisition position of the next tomographic image.

Also when the operation of automatic alignment for automatically adjusting the relative positional relationship between the subject's eye and an optical accommodation unit has been performed during capturing a tomographic image, similar distortion may occur in the tomographic image. Due to the eccentricity of the imaging optical axis caused by the automatic alignment, the retina in the tomographic image may be inclined or may move upward or downward. Particularly, if scanning has been performed a plurality of times to obtain a plurality of tomographic images, the captured retina may be positioned horizontally in one of the tomographic images, whereas the captured retina may be inclined in another tomographic image. If a plurality of captured tomographic images is different in inclination from each other as described above, the differences in inclination between the plurality of tomographic images appears as distortion in the shape of the retina in a three-dimensional image generated from the tomographic images.

These are specifically described in the following exemplary embodiments.

<Configurations of Optical Head Unit 100 and Spectrometer 200>

With reference to FIG. 1, the outline configuration of an optical coherence tomographic imaging apparatus according to a first exemplary embodiment is described. The optical coherence tomographic imaging apparatus acquires a tomographic image of a subject's eye based on interference light obtained by causing light reflected from the subject's eye irradiated with measurement light through a scanning unit, to interfere with reference light corresponding to the measurement light. The optical coherence tomographic imaging apparatus includes an optical head unit 100, a spectrometer 200, and a control unit 300. The configurations of the optical head unit 100, the spectrometer 200, and the control unit 300 are described in order below.

<Configurations of Optical Head Unit 100 and Spectrometer 200>

The optical head unit 100 includes a measurement optical system for capturing a two-dimensional image and a tomographic image of an anterior eye portion Ea of a subject's eye E and a fundus Er of the subject's eye E. The internal configuration of the optical head unit 100 is described below. An objective lens 101-1 is placed to be opposed to the subject's eye E. A first dichroic mirror 102 and a second dichroic mirror 103 are provided on the optical axis of the objective lens 101-1 and function as an optical path separation unit, thereby separating the optical path of the objective lens 101-1. More specifically, based on wavelength bands, the optical path branches into a measurement optical path L1 of an OCT optical system, an optical path L2 including the optical path for observing the fundus and the optical path of a fixation lamp, and an optical path L3 for observing the anterior eye portion.

Based on wavelength bands, the optical path L2 further branches by a third dichroic mirror 118 into the optical path of an avalanche photodiode (APD) 115 for observing the fundus and the optical path of a fixation lamp 116. On the optical path L2, lenses 101-2, 111, and 112 are placed. The lens 111 is driven by a motor (not illustrated) to adjust the focus for the fixation lamp 116 and the observation of the fundus Er. The APD 115 is sensitive to the wavelength of illuminating light for observing the fundus (not illustrated), specifically, sensitive to near 780 nm. On the other hand, the fixation lamp 116 generates visible light to prompt the subject to perform fixation.

Further, on the optical path L2, an X-scanner 117-1 (for a main scanning direction) and a Y-scanner 117-2 (for a sub-scanning direction, which intersects the main scanning direction) are placed. The X-scanner 117-1 and Y-scanner 117-2 are used to scan the fundus Er of the subject's eye E with light emitted from an illuminating light source for observing the fundus (not illustrated). The lens 101-2 is placed in such a manner that the focal position of the lens 101-2 is near each of the center positions of the X-scanner 117-1 and the Y-scanner 117-2. The X-scanner 117-1 is configured of a resonant mirror, but may be configured of a polygon mirror. The configuration is such that there is an optically conjugate relationship between the vicinity of each of the center positions of the X-scanner 117-1 and the Y-scanner 117-2 and the position of the pupil of the subject's eye E. Further, the APD 115 is a single detector and detects light returning from the fundus Er after being scattered and reflected by the fundus Er. The third dichroic mirror 118 is a prism on which a perforated mirror or a hollow mirror is vapor-deposited. The third dichroic mirror 118 separates the illuminating light and the light returning from the fundus Er.

On the optical path L3, a lens 141 and an infrared charge-coupled device (CCD) 142 for observing the anterior eye portion are placed. The infrared CCD 142 is sensitive to the wavelength of illuminating light for observing the anterior eye portion (not illustrated), specifically, sensitive to near 970 nm. The optical path L1 configures an OCT optical system as described above, and is used to capture a tomographic image of the fundus Er of the subject's eye E. More specifically, the optical path L1 is used to obtain an interference signal for forming a tomographic image.

On the optical path L1, a lens 101-3 and a mirror 121 are placed, and also an X-scanner 122-1 and a Y-scanner 122-2, which function as a scanning unit, are placed to scan the fundus Er of the subject's eye E with light. Further, the X-scanner 122-1 and the Y-scanner 122-2 are placed in such a manner that the focal position of the lens 101-3 is near each of the center positions of the X-scanner 122-1 and the Y-scanner 122-2. Further, there is an optically conjugate relationship between the vicinity of each of the center positions of the X-scanner 122-1 and the Y-scanner 122-2 and the position of the pupil of the subject's eye E. With this configuration, optical paths having object points at the scanning unit are approximately parallel to each other between the lenses 101-1 and 101-3. Thus, even if the X-scanner 122-1 and the Y-scanner 122-2 perform scanning, the incident angles on the first dichroic mirror 102 and the second dichroic mirror 103 can be the same.

Further, a measurement light source 130 is a light source for inputting measurement light in the measurement optical path L1. In the present exemplary embodiment, the measurement light source 130 is a fiber end and has an optically conjugate relationship with the fundus Er of the subject's eye E. On the measurement optical path L1, lenses 123 and 124 are placed. The lens 123 is driven by a motor (not illustrated) to adjust the focus. The focus is adjusted to form on the fundus Er an image of light emitted from the measurement light source 130, which is a fiber end. The lens 123, which functions as a focus adjustment unit, is placed between the measurement light source 130, and the X-scanner 122-1 and the Y-scanner 122-2, which function as the scanning unit. This eliminates the need to move the lens 101-3, which is larger than the lens 123, or an optical fiber 125-2.

With this focus adjustment, it is possible to form an image of light from the measurement light source 130 on the fundus Er of the subject's eye E, and also possible to efficiently return light returning from the fundus Er of the subject's eye E to the optical fiber 125-2 through the measurement light source 130.

In FIG. 1, the optical path between the X-scanner 122-1 and the Y-scanner 122-2 is configured on the plane of the paper, but in actuality is configured in a direction perpendicular to the plane of the paper. The optical head unit 100 further includes a head driving unit 140. The head driving unit 140 includes three motors (not illustrated) and is configured to move the optical head unit 100 in three-dimensional (X, Y, and Z) directions relative to the subject's eye E. This enables the alignment of the optical head unit 100 relative to the subject's eye E.

Next, an optical path from the measurement light source 130, a reference optical system, and the configuration of the spectrometer 200 are described. A Michelson interferometer is composed of the measurement light source 130, an optical coupler 125, optical fibers 125-1 to 125-4, a lens 151, dispersion-compensating glass 152, a mirror 153, and the spectrometer 200. The optical fibers 125-1 to 125-4 are single-mode optical fibers connected to the optical coupler 125 in an integrated manner.

Light emitted from the measurement light source 130 passes through the optical fiber 125-1 and is divided by the optical coupler 125 into measurement light on the optical fiber 125-2 side and reference light on the optical fiber 125-3 side. The measurement light passes through the optical path of the OCT optical system described above, and irradiates the fundus Er of the subject's eye E to be observed. Then, the measurement light is reflected and scattered by the retina and reaches the optical coupler 125 through the same optical path.

On the other hand, the reference light passes through the optical fiber 125-3, the lens 151, and the dispersion-compensating glass 152, which is inserted to balance the dispersion of the measurement light with the dispersion of the reference light. Then, the reference light reaches and is reflected from the mirror 153. Then, the reference light returns and reaches the optical coupler 125 through the same optical path. The optical coupler 125 combines the measurement light and the reference light to obtain interference light. Interference occurs when the optical path length of the measurement light and the optical path length of the reference light become substantially the same. The mirror 153 is held so that the position of the mirror 153 can be adjusted in the optical axis direction by a motor and a drive mechanism (not illustrated). This enables the mirror 153 to match the optical path length of the reference light to the optical path length of the measurement light, which varies depending on the subject's eye E. The interference light is guided to the spectrometer 200 through the optical fiber 125-4.

The spectrometer 200 includes a lens 201, a diffraction grating 202, a lens 203, and a line sensor 204. The interference light emitted from the optical fiber 125-4 becomes approximately parallel light through the lens 201 and is thereafter dispersed by the diffraction grating 202. Then, the lens 203 forms an image of the dispersed light on the line sensor 204.

Next, the periphery of the measurement light source 130 is described. The measurement light source 130 is a superluminescent diode (SLD), which is a typical low-coherent light source. The measurement light source 130 has a center wavelength of 855 nm and a wavelength bandwidth of about 100 nm. The bandwidth influences the resolution in the optical axis direction of a tomographic image to be obtained, and therefore is an important parameter. Further, although an SLD is selected as the type of the light source, the measurement light source 130 may only need to be able to emit low-coherent light, and therefore amplified spontaneous emission (ASE) may be used. Considering the measurement of the eye, near-infrared light is appropriate for the center wavelength. Further, the center wavelength influences the horizontal resolution of a tomographic image to be obtained. Thus, it is desirable that the center wavelength should be as short as possible. For both reasons, the center wavelength is set to 855 nm.

In the present exemplary embodiment, the interferometer is a Michelson interferometer, but may be a Mach-Zehnder interferometer. It is desirable to use a Mach-Zehnder interferometer if the difference in amount of light between the measurement light and the reference light is large, and to use a Michelson interferometer if the difference in amount of light between the measurement light and the reference light is relatively small.

<Configuration of Control Unit 300>

The control unit 300 is connected to the components of the optical head unit 100 and the spectrometer 200. More specifically, the control unit 300 is connected to the infrared CCD 142 in the optical head unit 100 and is configured to be able to generate an observation image of the anterior eye portion Ea of the subject's eye E. Further, the control unit 300 is also connected to the APD 115 in the optical head unit 100 and is also configured to be able to generate an observation image of the fundus Er of the subject's eye E. Further, the control unit 300 is also connected to the head driving unit 140 in the optical head unit 100 and is configured to be able to drive the optical head unit 100 three-dimensionally relative to the subject's eye E.

The control unit 300 is also connected to the line sensor 204 in the spectrometer 200. This enables the acquisition of measurement signals of light separated into wavelengths by the spectrometer 200, and also enables the generation of a tomographic image of the subject's eye E based on the measurement signals.

The observation image of the anterior eye portion Ea, the observation image of the fundus Er, and the tomographic image of the subject's eye E that have been generated can be displayed on a monitor 301 connected to the control unit 300.

<Method of Aligning Subject's Eye E>

Figure 2:
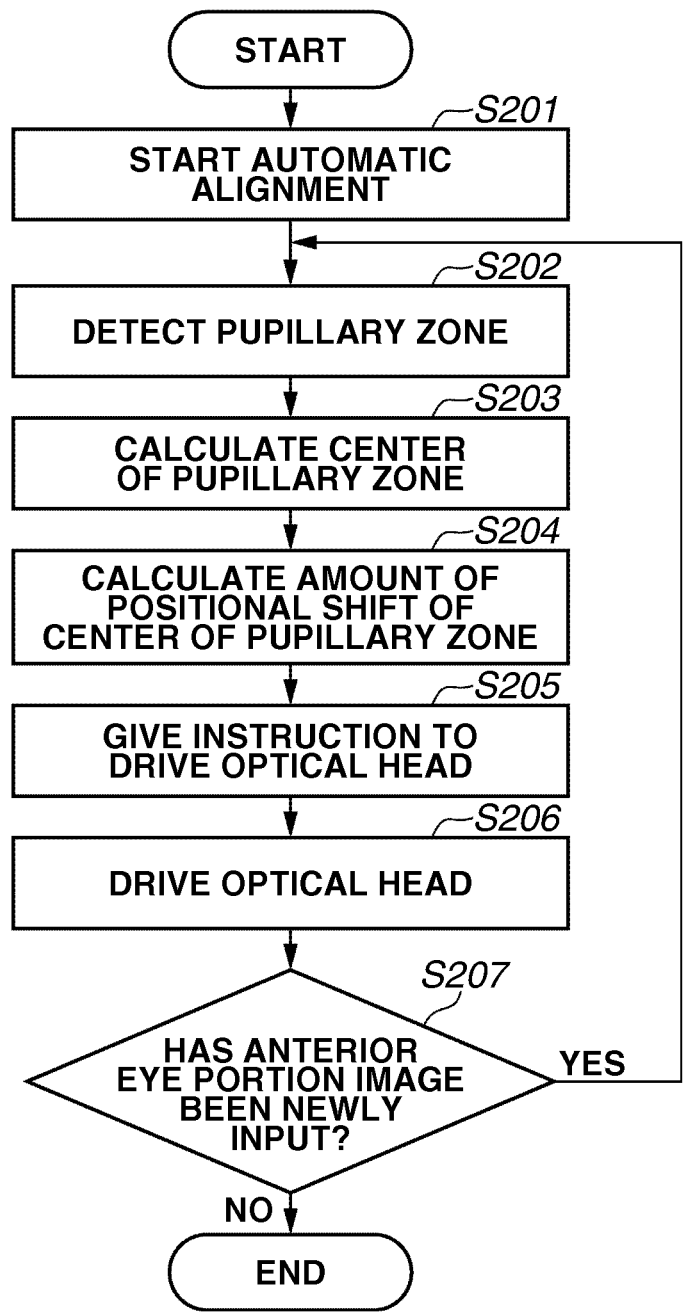
FIG. 2 is a flow chart illustrating an example of an automatic alignment operation according to the first exemplary embodiment.

Next, with reference to a flow chart in FIG. 2, a method of aligning the subject's eye E using the optical coherence tomographic imaging apparatus according to the first exemplary embodiment is described. Before capturing an image, an examiner first seats a subject in front of the apparatus.

In step S201, the control unit 300 receives an operation on a switch (not illustrated) performed by the examiner, and starts automatic alignment. In step S202, the control unit 300 functions as an anterior eye portion image acquisition unit. If the automatic alignment has been started, the control unit 300 periodically acquires an anterior eye portion image from the infrared CCD 142 and analyzes the anterior eye portion image. More specifically, the control unit 300 detects a pupillary region in an input anterior eye portion image.

In step S203, the control unit 300 calculates the center position of the detected pupillary region. In step S204, the control unit 300 functions as a positional shift amount calculation unit and calculates the amount of displacement (the amount of positional shift) between the center position of the detected pupillary region and the center position of the anterior eye portion image. The optical coherence tomographic imaging apparatus according to the present exemplary embodiment is configured in such a manner that the center of an anterior eye portion image coincides with the optical axis of the objective lens 101-1. Thus, the amount of displacement calculated in step S204 represents the amount of positional shift between the subject's eye E and the measurement optical axis.

In step S205, the control unit 300 instructs the head driving unit 140 to move the optical head unit 100 according to the amount of positional shift calculated in step S204. In step S206, the head driving unit 140 drives the three motors (not illustrated) to move the position of the optical head unit 100 in the three-dimensional (X, Y, and Z) directions relative to the subject's eye E. As a result of the movement, the position of the optical axis of the objective lens 101-1 mounted on the optical head unit 100 is corrected to approximate the center position of the pupil of the anterior eye portion Ea of the subject's eye E.

In step S207, the control unit 300 determines whether or not, after the movement of the optical head unit 100, an anterior eye portion image has been newly input from the infrared CCD 142. If it is determined that an anterior eye portion image has been newly input (YES in step S207), the processing returns to step S202. If, on the other hand, it is determined that an anterior eye portion image has not been newly input (NO in step S207), the processing ends.

Through the series of steps in the automatic alignment operation, the position of the optical axis of the objective lens 101-1 moves to always track the center position of the pupil of the anterior eye portion Ea of the subject's eye E. Even if the line-of-sight direction of the subject's eye E has changed, the automatic alignment operation causes the optical axis of the objective lens 101-1 to track the center of the pupil of the anterior eye portion Ea (anterior eye portion tracking) after the change in the line of sight. Thus, the measurement light beam emitted from the measurement light source 130 irradiates the fundus Er without being blocked by the pupil. This enables stable capturing of a tomographic image.

Then, the series of steps in the automatic alignment operation continue until the scanning of the fundus portion Er of the subject's eye E with the measurement light is started to record tomographic images of the fundus portion Er of the subject's eye E.

In the present exemplary embodiment, the automatic alignment of an optical system relative to a subject's eye is performed based on an anterior eye portion image obtained using an infrared CCD, but may be carried out using another technique. For example, a mark for alignment is projected onto an anterior eye portion of a subject's eye, and light reflected from the anterior eye portion is detected. This enables automatic alignment in the three-dimensional (X, Y, and Z) directions.

<Method of Tracking Fundus>

Figure 3:
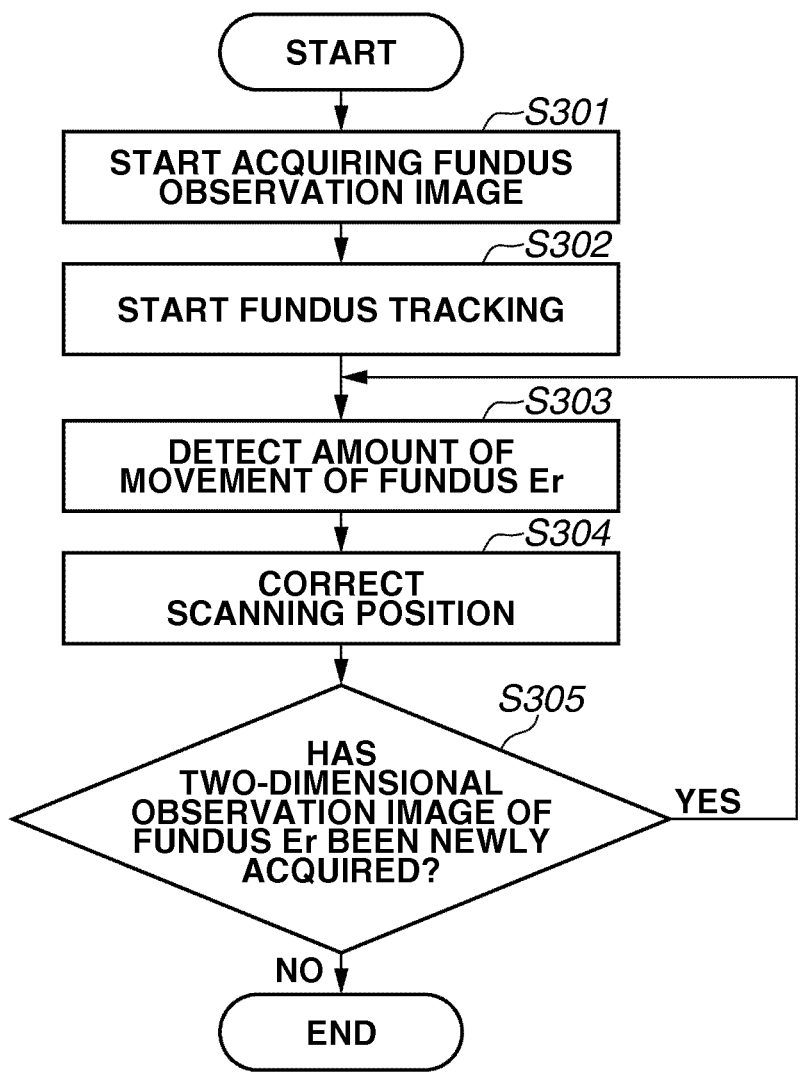
FIG. 3 is a flow chart illustrating an example of a fundus tracking operation according to the first exemplary embodiment.

Next, with reference to a flow chart in FIG. 3, a method of tracking the fundus for correcting a shift occurring in the irradiation position of the measurement light due to the movement of the subject's eye E when irradiating the fundus portion Er of the subject's eye E with the measurement light to observe the state of the subject's eye E, is described.

In step S301, after the start of the automatic alignment operation described above, the control unit 300 starts the operation of acquiring a two-dimensional observation image of the fundus Er through the optical path L2. More specifically, the control unit 300 starts acquiring light reflected from the fundus Er, which is input from the APD 115. The light reflected from the fundus Er is two-dimensionally scanned continuously by the X-scanner 117-1 and the Y-scanner 117-2. Thus, the reflected light input from the APD 115 is periodically combined, whereby it is possible to periodically obtain an observation image of the fundus Er.

In step S302, the control unit 300 starts a fundus tracking operation based on the periodically acquired fundus observation image. In step S303, the control unit 300 calculates the amount of movement of the fundus Er using two fundus observation images, namely the previously acquired fundus observation image and the current fundus observation image. More specifically, the control unit 300 calculates the amount of displacement of a region of interest in two-dimensional (X and Y) directions on the fundus observation images, thereby calculating the amount of movement of the fundus Er in the two-dimensional (X and Y) directions. The control unit 300 is an example of a movement amount acquisition unit configured to, based on a plurality of images (e.g., a plurality of fundus images) of a subject's eye acquired at different times, acquire the amount of movement of the subject's eye. The region of interest is a macula, an optic papilla, or a vessel bifurcation on the fundus Er, and may be any region on the fundus Er so long as the amount of movement of the fundus Er can be calculated.

In step S304, according to the calculated amount of movement of the fundus Er, the control unit 300 controls the X-scanner 122-1 and the Y-scanner 122-2 to correct the scanning position to always irradiate the same area on the fundus Er with the measurement light through the optical path L1.

In step S305, the control unit 300 determines whether a two-dimensional observation image of the fundus Er has been newly acquired. If it is determined that a two-dimensional observation image of the fundus Er has been newly acquired (YES in step S305), the processing returns to step S303. If, on the other hand, it is determined that a two-dimensional observation image of the fundus Er has not been newly acquired (NO in step S305), the processing ends.

Through the series of steps in the fundus tracking operation, the measurement light emitted from the measurement light source 130 to the fundus Er moves to always track the movement of the fundus Er of the subject's eye. This enables stable capturing of a tomographic image. Then, the series of steps in the fundus tracking operation are continuously performed until the examination of the subject's eye E is ended.

In the present exemplary embodiment, fundus tracking is performed using a fundus observation image obtained by a point-scanning-type scanning laser ophthalmoscope (SLO), but may be carried out using another technique. For example, fundus tracking can be performed using a two-dimensional fundus observation image acquired by combining infrared light capable of widely irradiating the fundus, and an infrared CCD. Alternatively, any pattern formed by a light source is projected onto a fundus, and fundus tracking can be performed using the light reflected from the fundus.

<Method of Capturing Tomographic Image>

Next, a method of capturing tomographic images using the optical coherence tomographic imaging apparatus according to the first exemplary embodiment is described.

The examiner operates a switch (not illustrated) on the control unit 300 to start capturing an image. In response to an instruction to start capturing an image, the control unit 300 starts generating tomographic images for recording generated based on interference light signals periodically output from the line sensor 204.

The interference light signals output from the line sensor 204 is signals of respective frequencies obtained by the diffraction grating 202 dispersing light. The control unit 300 performs a fast Fourier transform (FFT) process on the signals output from the line sensor 204 to generate information of the fundus Er in the depth direction at a certain point. The generation of information of the fundus Er in the depth direction at a certain point is referred to as an "A-scan".

Then, the measurement light irradiating the fundus Er can optionally scan the fundus Er by controlling the driving of at least one of the X-scanner 122-1 and the Y-scanner 122-2. The X-scanner 122-1 and the Y-scanner 122-2 can scan the subject's eye E with the measurement light.

The control unit 300 combines a series of A-scans acquired while the scanning along the optional trajectory is performed once, into a single two-dimensional image, thereby generating a tomographic image of the fundus Er along the optional trajectory.

Further, the control unit 300 controls the driving of at least one of the X-scanner 122-1 and the Y-scanner 122-2, thereby repeating the scanning along the optional trajectory a plurality of times. If scanning along the same trajectory has been performed a plurality of times, it is possible to obtain a plurality of tomographic images along an optional trajectory on the fundus Er. For example, the control unit 300 drives only the X-scanner 122-1 to repeatedly execute scanning in the X-direction, thereby generating a plurality of tomographic images along the same scan line on the fundus Er. Alternatively, the control unit 300 can also simultaneously drive the X-scanner 122-1 and the Y-scanner 122-2 to repeatedly execute circular scanning, thereby generating a plurality of tomographic images along the same circle on the fundus Er. Then, the control unit 300 performs an averaging process on the plurality of tomographic images to generate a single high-quality tomographic image, and displays the generated tomographic image on the monitor 301.

On the other hand, the control unit 300 controls the driving of at least one of the X-scanner 122-1 and the Y-scanner 122-2, and thereby can perform scanning a plurality of times while shifting the scanning along the optional trajectory as described above in the X and Y directions. For example, the control unit 300 performs scanning in the X-direction a plurality of times while shifting the scanning in the Y-direction at regular intervals, thereby generating a plurality of tomographic images that covers the entire rectangular area on the fundus Er. Then, the control unit 300 combines the plurality of tomographic images to generate three-dimensional information of the fundus Er, and displays the generated image on the monitor 301.

It is possible to optionally switch between the scanning patterns of the X-scanner 122-1 and the Y-scanner 122-2 by pressing a scanning pattern selection button (not illustrated).

<Automatic Alignment Control During Capturing Tomographic Images>

When scanning is performed a plurality of times as described above to capture a plurality of tomographic images, it takes a longer time to perform the scanning a plurality of times than performing a single scan. For example, the optical coherence tomographic imaging apparatus according to the first exemplary embodiment shifts, in the Y-direction by 0.078 mm each time, a scan of 10 mm in the X-direction on the fundus Er, and thereby can repeat scanning 128 times. Then, the optical coherence tomographic imaging apparatus can acquire 128 tomographic images by performing the scanning 128 times, and generate three-dimensional information of the fundus Er in a range of 10 mm×10 mm. In the optical coherence tomographic imaging apparatus according to the present exemplary embodiment, a single tomographic image is composed of a total of 1024 A-scans, and it takes 14.3 microseconds to perform a single A-scan. Thus, it takes 1024×14.3 microseconds=14.6 milliseconds to obtain a single tomographic image, and therefore, it takes at least 14.6 milliseconds per image×128 images=1.87 seconds to obtain all 128 tomographic images.

Meanwhile, human eyeball movements can be broadly divided into three types (saccade, drift, and tremor). These eyeball movements are types of involuntary movements. Even if the subject is gazing at a fixation lamp, it is difficult to completely suppress these eyeball movements. Further, the cycle of occurrence of such an eyeball movement is shorter than the capturing period described above (i.e., 1.87 seconds). Thus, these eyeball movements often occur a plurality of times while scanning is performed a total of 128 times.

Figure 4:
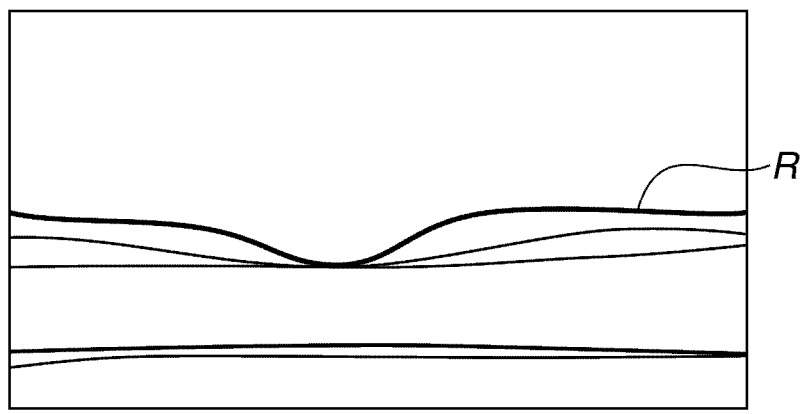
FIG. 4 is a diagram illustrating an example of a tomographic image captured in an appropriate state of alignment, according to the first exemplary embodiment.
Figure 5:
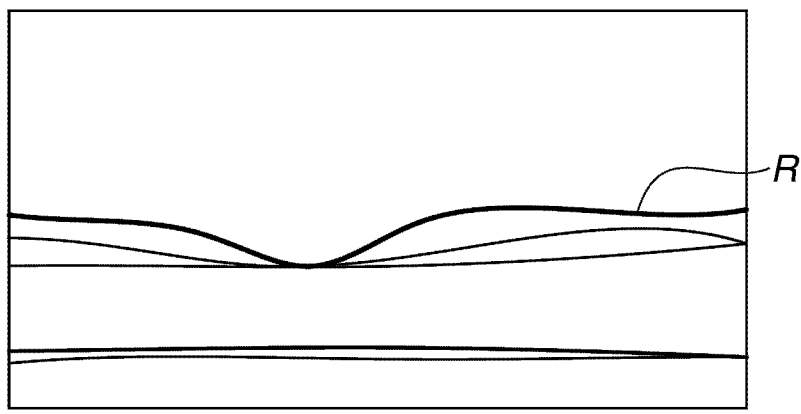
FIG. 5 is a diagram illustrating an example of a tomographic image captured with an eyeball movement having occurred, according to the first exemplary embodiment.

However, the changes in the position of the pupil due to these eyeball movements do not have such a great influence on a tomographic image to be captured. FIG. 4 is an example of a tomographic image captured with the center of the pupil of the anterior eye portion Ea of the subject's eye E coinciding with the optical axis of the objective lens 101-1. On the other hand, FIG. 5 is an example of a tomographic image captured with the center of the pupil shifted about 1 mm in the X-direction relative to the optical axis of the objective lens 101-1. The tomographic image of the fundus Er illustrated in FIG. 5 is captured with a retina R shifted in the X-direction relative to the retina R in the tomographic image in FIG. 4. The tomographic image itself, however, is not greatly deformed. Further, such a shift in the X-direction can be corrected based on the fundus tracking described above.

Figure 6:
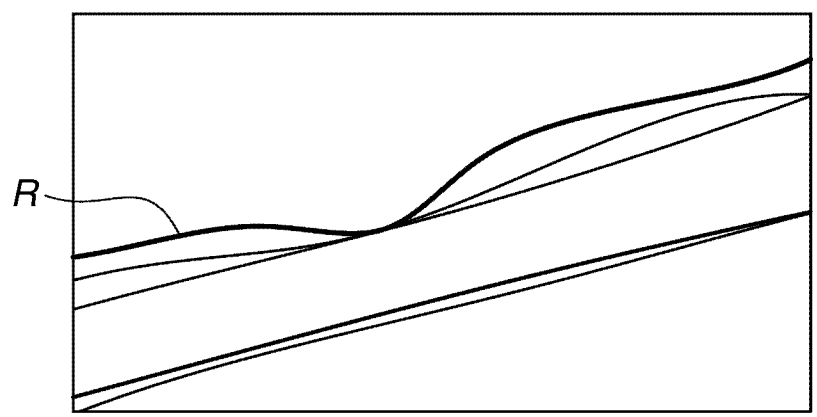
FIG. 6 is a diagram illustrating an example of a tomographic image captured during the operation of automatic alignment, according to the first exemplary embodiment.
Figure 7:
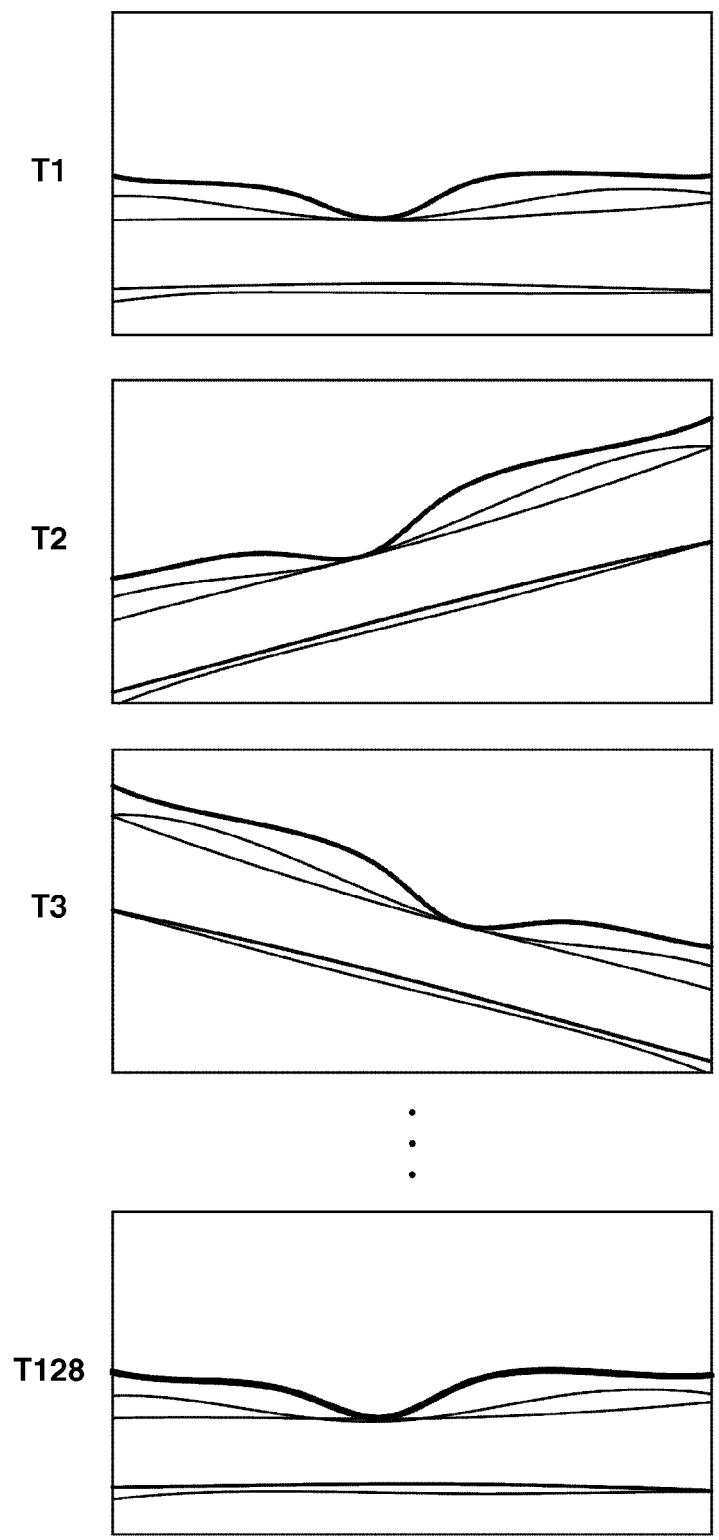
FIG. 7 is a diagram illustrating examples of a plurality of tomographic images captured during the operation of automatic alignment, according to the first exemplary embodiment.
Figure 8:
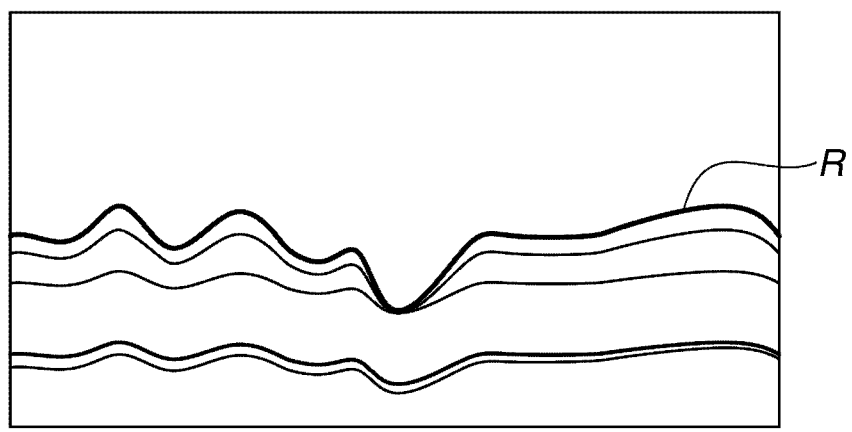
FIG. 8 is a diagram illustrating an example of a virtual tomographic image generated from the plurality of tomographic images illustrated in FIG. 7.

In contrast, if the operation of automatic alignment has been performed according to eyeball movements, a tomographic image to be captured is greatly influenced. FIG. 6 is an example of a tomographic image captured by performing the operation of automatic alignment with respect to the state of FIG. 5 so that the center of the pupil coincides with the optical axis of the objective lens 101-1. It is understood that as compared to the tomographic image in FIG. 4, not only does a shift occur in the X-direction, but also the retina R is greatly inclined. Such inclination of the retina R cannot be corrected based on the fundus tracking. Further, if the operation of automatic alignment has been performed while scanning is performed a total of 128 times, the inclination of the retina R significantly changes during the capturing of 128 tomographic images as illustrated in FIG. 7. Such changes in the inclination cause a significant problem particularly in a three-dimensional image generated by reconstructing a plurality of tomographic images. FIG. 8 is an example where the 128 tomographic images illustrated in FIG. 7 are reconstructed to display a virtual cross-sectional image orthogonal to the main scanning direction. It is understood that the shape of the retina R is greatly deformed in the virtual cross-sectional image. When an ophthalmologist makes a diagnosis of an eye disease based on the shape of the retina R, the changes in the inclination of the retina R may not only hinder the diagnosis, but also lead to a misdiagnosis.

Thus, the optical coherence tomographic imaging apparatus according to the present exemplary embodiment performs a process of temporarily stopping the operation of automatic alignment while scanning is executed to capture a plurality of tomographic images. With reference to a flow chart in FIG. 9, this operation is described below. Before capturing an image, the examiner first seats the subject in front of the apparatus. The control unit 300 controls the driving of at least one of the X-scanner 122-1 and the Y-scanner 122-2, which function as the scanning unit. Thus, the at least one of the X-scanner 122-1 and the Y-scanner 122-2 can execute observation scanning for obtaining an observation tomographic image for observing the state of the subject's eye, and recording scanning for obtaining a recording tomographic image for recording the state of the subject's eye, by switching between the observation scanning and the recording scanning.

In step S901, the control unit 300 receives an operation on a switch (not illustrated) performed by the examiner, and starts automatic alignment. In step S902, the control unit 300 starts acquiring an observation tomographic image of the fundus Er to observe the state of alignment.

In step S903, the control unit 300 displays the acquired observation tomographic image on the monitor 301. With reference to the observation tomographic image displayed on the monitor 301, the examiner can determine whether the state of alignment is favorable. If the examiner has determined that the state of alignment is favorable, the examiner operates a switch (not illustrated) on the control unit 300 to instruct the control unit 300 to start capturing tomographic images.

In step S904, in response to the operation on the switch (not illustrated) performed by the examiner, the control unit 300 starts capturing recording tomographic images. If the control unit 300 has been instructed to start capturing tomographic images, then in step S905, the control unit 300 stops the operation of the automatic alignment before the capturing of recording tomographic images.

In step S906, the control unit 300 starts scanning for generating recording tomographic images. More specifically, the control unit 300 controls the driving of at least one of the X-scanner 122-1 and the Y-scanner 122-2, thereby executing scanning along an optional trajectory a plurality of times.

Figure 9:
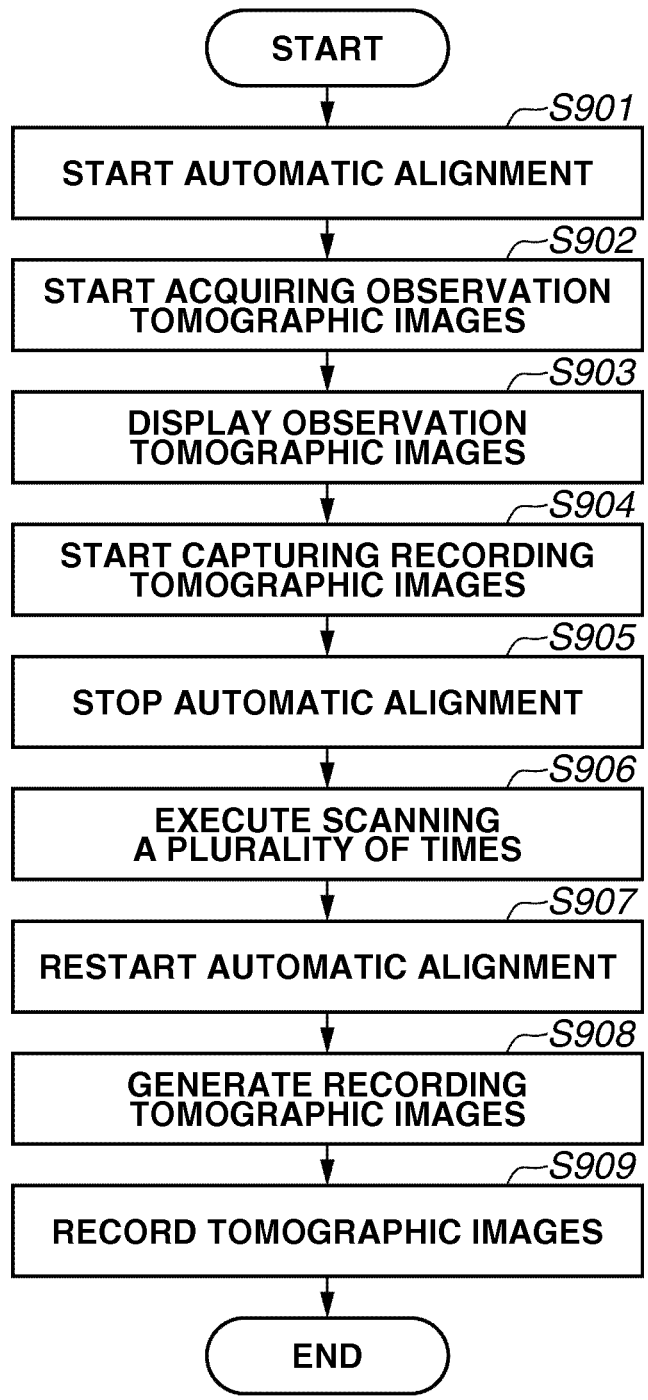
FIG. 9 is a flow chart illustrating an example of automatic alignment control according to the first exemplary embodiment.

In step S907, after the completion of all the scans, the control unit 300 restarts the operation of the automatic alignment. In step S908, the control unit 300 generates a plurality of tomographic images corresponding to the plurality of scans. In step S909, the control unit 300 records the plurality of tomographic images generated in step S908 in a recording medium (not illustrated). Then, the processing of the flow chart in FIG. 9 is ended.

In the present exemplary embodiment, the automatic alignment is stopped immediately before the scanning for acquiring recording tomographic images is started. Alternatively, the automatic alignment may be stopped at a time before the above time. More specifically, the operation of the automatic alignment may be stopped when it is determined that the position of the pupil of the subject's eye has approximately coincided with the optical axis of the optical system by the automatic alignment.

A reception unit configured to receive a signal for acquiring a plurality of tomographic images may be further provided. The processing may be started after the reception of the signal.

As described above, the optical coherence tomographic imaging apparatus according to the present exemplary embodiment stops the operation of automatic alignment at least when generating recording tomographic images, and thereby can obtain a suitable tomographic image with reduced deformation.

<Fundus Tracking Control During Capturing Tomographic Images>

Also if fundus tracking has been performed while scanning for acquiring a single tomographic image is being performed, a tomographic image to be captured is greatly influenced. As described above, in the optical coherence tomographic imaging apparatus according to the present exemplary embodiment, it takes 14.6 milliseconds to obtain a single tomographic image. Thus, to capture a plurality of tomographic images, the fundus Er is scanned a plurality of times with a cycle of about 14.6 milliseconds. This cycle depends on the number of A-scans required for forming a single tomographic image and also on the time required for acquiring a single A-scan. Meanwhile, in the optical coherence tomographic imaging apparatus according to the present exemplary embodiment, the scanning position is corrected based on fundus tracking on a cycle of 33.3 milliseconds. This cycle depends on the acquisition interval of an observation image of the fundus Er for use in calculating the amount of positional shift for the correction.

Figure 10:
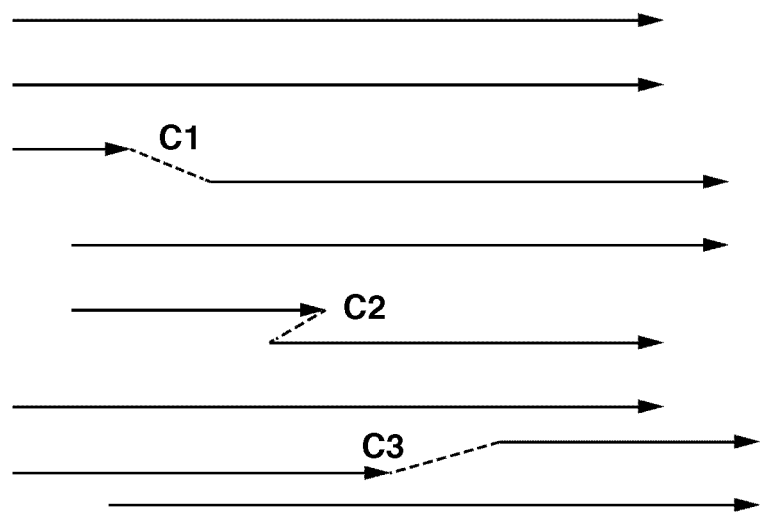
FIG. 10 is a diagram illustrating examples of scanning patterns without fundus tracking control according to the first exemplary embodiment.
Figure 11:
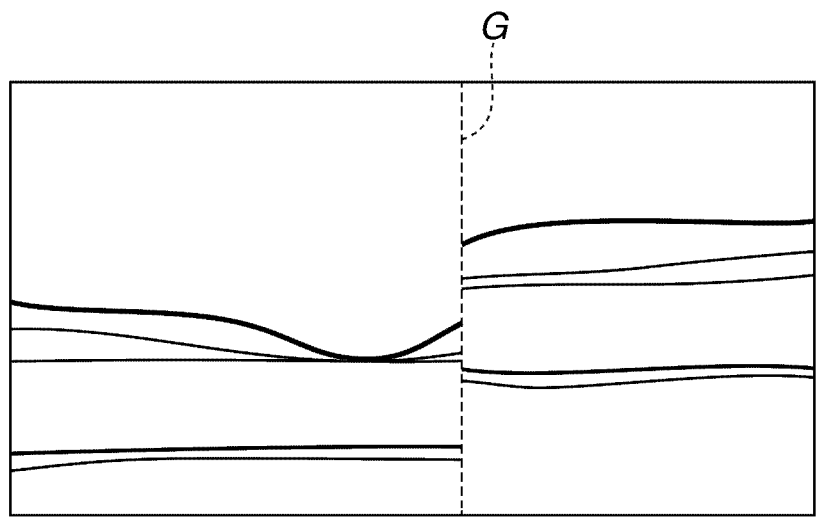
FIG. 11 is a diagram illustrating an example of a tomographic image obtained by the scanning illustrated in FIG. 10.

If the acquisition interval of a tomographic image and the acquisition interval of a fundus observation image are thus different from each other, then as illustrated in FIG. 10, a correction $C_i$ ($i=1$ to 3) of the scanning position based on the fundus tracking is performed while the fundus Er is being scanned to obtain a single tomographic image. Further, while the correction interval of the scanning position based on fundus tracking is long, the time required for the actual correction is very short. Thus, the correction of the scanning position based on fundus tracking is an operation of instantly correcting the scanning position according to all eyeball movements made within the correction interval. Thus, if the scanning position has been corrected based on the fundus tracking while the fundus Er is being scanned to obtain a single tomographic image, a gap G in the retinal layers appears as illustrated in FIG. 11. When an ophthalmologist performs a diagnosis of an eye disease based on the shapes of the retinal layers, the gap G in the retinal layers may not only hinder the diagnosis, but also lead to a misdiagnosis.

On the other hand, when capturing a plurality of tomographic images, the optical coherence tomographic imaging apparatus according to the present exemplary embodiment corrects the scanning position based on fundus tracking between scans for obtaining the respective tomographic images, and stops the correction during the scans. With reference to a flow chart in FIG. 12, this operation is described below. Before capturing an image, the examiner first seats the subject in front of the apparatus. The control unit 300 controls the driving of at least one of the X-scanner 122-1 and the Y-scanner 122-2, which function as the scanning unit. Then, the at least one of the X-scanner 122-1 and the Y-scanner 122-2 can execute observation scanning for obtaining an observation tomographic image for observing the state of the subject's eye, and recording scanning for obtaining a recording tomographic image for recording the state of the subject's eye, by switching between the observation scanning and the recording scanning.

In step S1201, the control unit 300 receives an operation on a switch (not illustrated) performed by the examiner, and starts automatic alignment. Then, the control unit 300 starts acquiring an observation tomographic image of the fundus Er to observe the state of alignment. In step S1202, the control unit 300 displays the acquired observation tomographic image on the monitor 301. With reference to the observation tomographic image displayed on the monitor 301, the examiner can determine whether the state of alignment is favorable.

In step S1203, according to the fact that the examiner has determined that the state of alignment is favorable and the control unit 300 has received an operation on a switch (not illustrated) on the control unit 300, the control unit 300 starts capturing recording tomographic images. To adjust the coherence gate, in steps S1201 to S1203, the scanning position may be corrected based on fundus tracking.

In step S1204, the control unit 300 controls the driving of at least one of the X-scanner 122-1 and the Y-scanner 122-2, which function as the scanning unit, thereby starting a single scan along an optional trajectory.

In step S1205, the control unit 300 functions as a fundus image acquisition unit and determines whether a captured fundus image has been acquired. If it is determined that a fundus image has been acquired (YES in step S1205), the processing proceeds to step S1206. If, on the other hand, it is determined that a fundus image has not been acquired (NO in step S1205), the processing proceeds to step S1208.

In step S1206, the control unit 300 functions as a movement amount calculation unit and calculates the amount of movement of the fundus Er based on an already acquired fundus image and the newly acquired fundus image.

In step S1207, the control unit 300 stores, in a memory (not illustrated), information indicating that the movement of the fundus Er has been detected during the currently executed single scan, and information indicating the detected amount of movement of the fundus Er. Thereafter, the processing proceeds to step S1208. In step S1208, the control unit 300 ends the single scan.

In step S1209, according to the information stored in the memory (not illustrated), the control unit 300 determines whether the movement of the fundus Er has been detected during the execution of the single scan. If it is determined that the movement of the fundus Er has been detected (YES in step S1209), the processing proceeds to step S1210. If, on the other hand, it is determined that the movement of the fundus Er has not been detected (NO in step S1209), the processing proceeds to step S1212.

In step S1210, the control unit 300 reads the calculated amount of movement from the memory (not illustrated). In step S1211, the control unit 300 calculates a next scanning start position corrected by offsetting the amount of movement of the fundus Er, and moves the next scanning position to the offset scanning start position.

In step S1212, the control unit 300 controls the driving of at least one of the X-scanner 122-1 and the Y-scanner 122-2, which function as the scanning unit, thereby moving the scanning position to a next scanning start position.

In step S1213, the control unit 300 determines whether the entire series of scans have ended. If it is determined that the entire series of scans have ended (YES in step S1213), the processing proceeds to step S1214. If, on the other hand, it is determined that there is a next scan yet to be performed (NO in step S1213), the processing returns to step S1204, and the series of steps in the fundus tracking operation are repeated.

Figure 12:
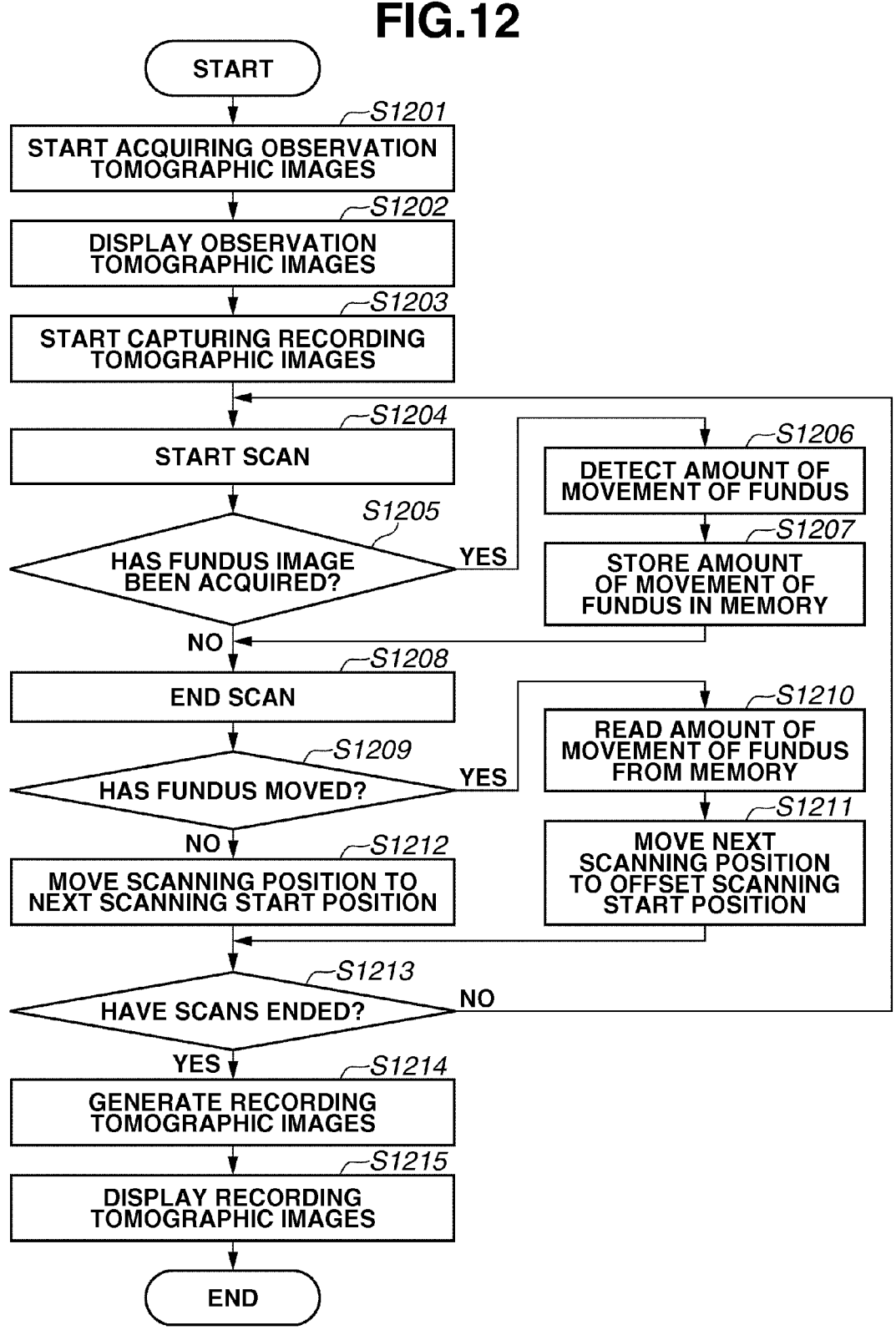
FIG. 12 is a flow chart illustrating an example of fundus tracking control according to the first exemplary embodiment.

In step S1214, the control unit 300 generates a plurality of recording tomographic images corresponding to the series of scans. In step S1215, the control unit 300 displays the recording tomographic images generated in step S1214 on the monitor 301. Then, the processing of the flow chart in FIG. 12 is ended. As described above, the correction of the scanning position is stopped during a single scan, and the scanning position is corrected between the single scan and the next scan. Further, the control unit 300 may control the scanning unit to correct the scanning position during the sub-scanning performed by the scanning unit, and also to stop correcting the scanning position during the main scanning performed by the scanning unit.

Figure 13:
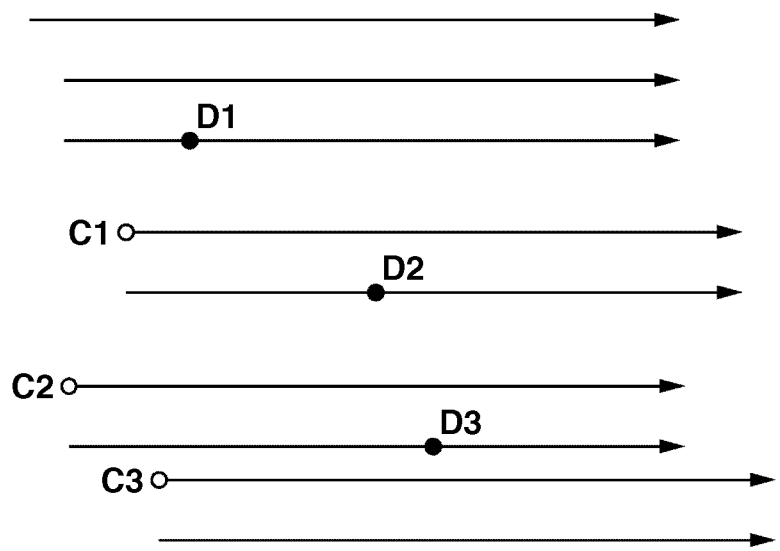
FIG. 13 is a diagram illustrating examples of scanning patterns when fundus tracking control is performed, according to the first exemplary embodiment.

With reference to FIG. 13, a description is given of an example of scanning when the fundus Er is scanned a plurality of times while fundus tracking is performed, according to the flow chart in FIG. 12. The movement of the fundus Er is detected at a time Di (i=1 to 3), and the scanning position is corrected based on the calculated amount of movement at a time Ci (i=1 to 3). As illustrated in FIG. 13, the correction of the scanning position according to the movement of the fundus Er detected at a time D1 is delayed until the start of the next scan, which is indicated by a time C1. Similarly, the correction of the scanning position according to the movement of the fundus Er detected at a time D2 is delayed until a time C2, and the correction of the scanning position according to the movement of the fundus Er detected at a time D3 is delayed until a time C3. By such control, all the scans of the fundus Er of the subject's eye are continuously performed to the end without interruption. This can make it less likely that the gap G in the retinal layers as illustrated in FIG. 11 appears on a captured recording tomographic image. The scanning position is not corrected for the tomographic image obtained by the scans at the times D1, D2, and D3 when the movement of the fundus Er has been detected. Thus, it is unlikely that the gap G in the retinal layers appears. The fundus Er, however, is moving during the scans, and therefore, some distortion may occur in the obtained tomographic image. Thus, the tomographic image obtained by the scans at the times D1, D2, and D3 may be eliminated, or a new tomographic image may be captured by performing similar scans at the respective scanning positions again. This enables the acquisition of a tomographic image with further reduced distortion.

In the processing of the flow chart in FIG. 12, also the process of stopping the automatic alignment and the process of restarting the automatic alignment, which are described in steps S905 and S907 in FIG. 9, may be executed in parallel. More specifically, the process of stopping the alignment, which is described in step S905, may be additionally executed between the processes of steps S1203 and S1204, and the process of restarting the alignment, which is described in step S907, may be additionally executed between the processes of steps S1213 and S1214. As described above, at least one of the process regarding automatic alignment in FIG. 9 and the process of correcting the scanning position based on fundus tracking in FIG. 12 may be executed.

In the present exemplary embodiment, when recording tomographic images are acquired, control is performed so that the scanning position is corrected between scans (between a single scan and a next scan). Alternatively, also when an observation tomographic image is acquired, similar control may be carried out. In this case, it is possible to also reduce distortion in the retinal layers in the observation tomographic image. Yet alternatively, when an observation tomographic image is acquired, the scanning position may not be corrected between scans (between a single scan and a next scan), but may be corrected when the movement of the fundus Er has been detected. An observation tomographic image is displayed as a real-time observation moving image, and therefore is displayed for a very short period. Further, an observation tomographic image is not used for a diagnosis, and therefore, some distortion in the retinal layers is tolerable.

As described above, the optical coherence tomographic imaging apparatus according to the present exemplary embodiment stops, during the execution of scanning, at least one of the alignment of an optical system for capturing a subject's eye relative to the subject's eye, and the correction of the scanning position based on the fundus tracking of the subject's eye. Thus, it is possible to obtain a tomographic image with reduced distortion.

<Detect Amount of Rotation of Fundus>

Next, a second exemplary embodiment is described. The configuration of the apparatus is similar to that of the first exemplary embodiment, and therefore is not described below. The alignment of the subject's eye, the tracking of the fundus, and the acquisition of a tomographic image are performed similarly to those according to the first exemplary embodiment.

The present exemplary embodiment is different from the first exemplary embodiment in that the amount of rotation of the fundus is also detected in addition to the amount of movement of the fundus. In the first exemplary embodiment, the amount of movement in the X-direction and the Y-direction is detected to correct the scanning position. Thus, if the angle of the subject's eye has changed during the scanning, a tomographic image may not be linear on the fundus. Therefore, the amount of rotation of the fundus is detected to correct the rotational direction of the scanning.

Specifically, the amount of rotation of the fundus is detected as follows. Regions of interest are provided at two locations on a fundus observation image, and the regions of interest are detected in each of the previous fundus observation image and the current fundus observation image. The coordinates of the regions of interest detected in the previous fundus observation image are represented as A1(xa1, ya1) and B1(xb1, yb1). The coordinates of the regions of interest detected in the current fundus observation image are represented as A2(xa2, ya2) and B2(xb2, yb2). The region of interest A2 is the same as the region of interest A1, and the region of interest B2 is the same as the region of interest B1.

Generally, the transformation of coordinates with a combination of the translation and the rotation of two-dimensional coordinates is represented by an affine transformation matrix. The transformation from the coordinates of the previous fundus observation image to the coordinates of the current fundus observation image is performed by the following procedure. First, the region of interest A1 is translated to coincide with the origin (0, 0). This translation is represented by a vector (tx1, ty1). Next, a vector A1B1 (xb1−xa1, yb1−ya1) is rotated about the origin (=A1) to coincide with a vector A2B2 (xb2−xa2, yb2−ya2). This angle of rotation is represented as θ. Finally, the region of interest A2 is translated to coincide with the origin (=A1). This translation is represented by a vector (tx2, ty2). The above procedure is represented by the following affine transformation.

$$\begin{pmatrix} x' \\ y' \\ 1 \end{pmatrix} = \begin{pmatrix} 1 & 0 & tx2 \\ 0 & 1 & ty2 \\ 0 & 0 & 1 \end{pmatrix} \begin{pmatrix} \cos\theta & -\sin\theta & 0 \\ \sin\theta & \cos\theta & 0 \\ 0 & 0 & 1 \end{pmatrix} \begin{pmatrix} 1 & 0 & tx1 \\ 0 & 1 & ty1 \\ 0 & 0 & 1 \end{pmatrix} \begin{pmatrix} x \\ y \\ 1 \end{pmatrix} \quad \text{Formula 1}$$

In the formula 1, the coordinates before the transformation are represented as (x, y), and the coordinates to be obtained after the transformation are represented as (x', y'). The coordinates transformation is performed for all the scans from the next scan and thereafter, using this coordinate transformation matrix.

Figure 18:
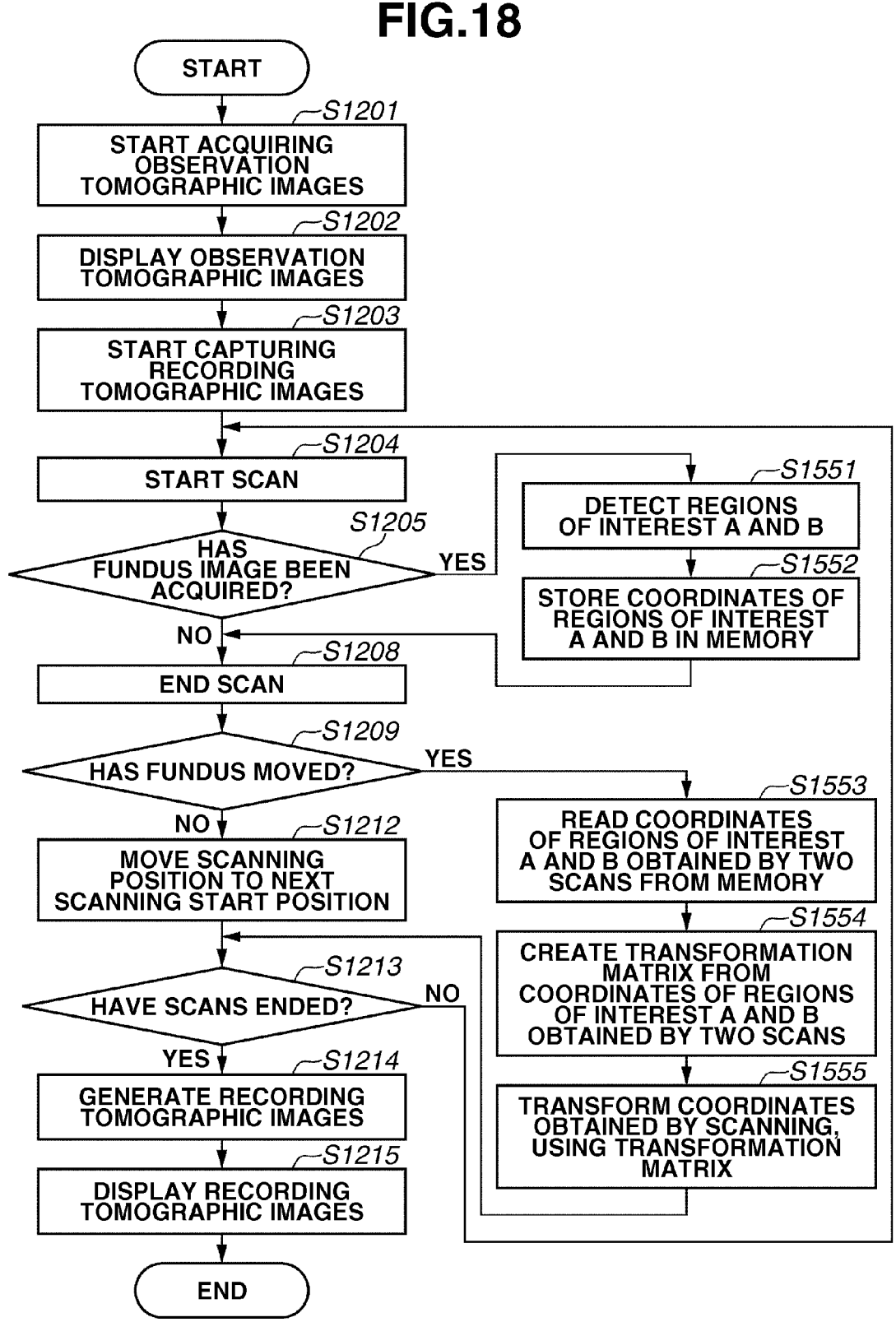
FIG. 18 is a flow chart according to a second exemplary embodiment, in which the correction of the amount of rotation is added.

FIG. 18 is a flow chart in which the correction based on the amount of rotation is added. FIG. 18 is almost similar to FIG. 12 except that the creation and the application of a coordinate transformation matrix are performed using an affine transformation based on the regions of interest A and B. If a fundus image has been acquired, then in step S1551, the control unit 300 detects the regions of interest A and B. In step S1552, the control unit 300 stores the coordinates of the detected regions of interest A and B in a memory. In step S1553, the control unit 300 reads from the memory the coordinates (A1, B1, A2, and B2) of the regions of interest A and B obtained by two scans. In step S1554, the control unit 300 creates a transformation matrix from the coordinates read in step S1553, using an affine transformation by the above procedure. In step S1555, the control unit 300 transforms the coordinates obtained by the next scan and thereafter, using the created transformation matrix. Thus, it is possible to continue scanning so that the trajectory of the scanning is linear on the fundus.

<Determine Whether Amount of Rotation of Fundus Exceeds Threshold>

Figure 14:
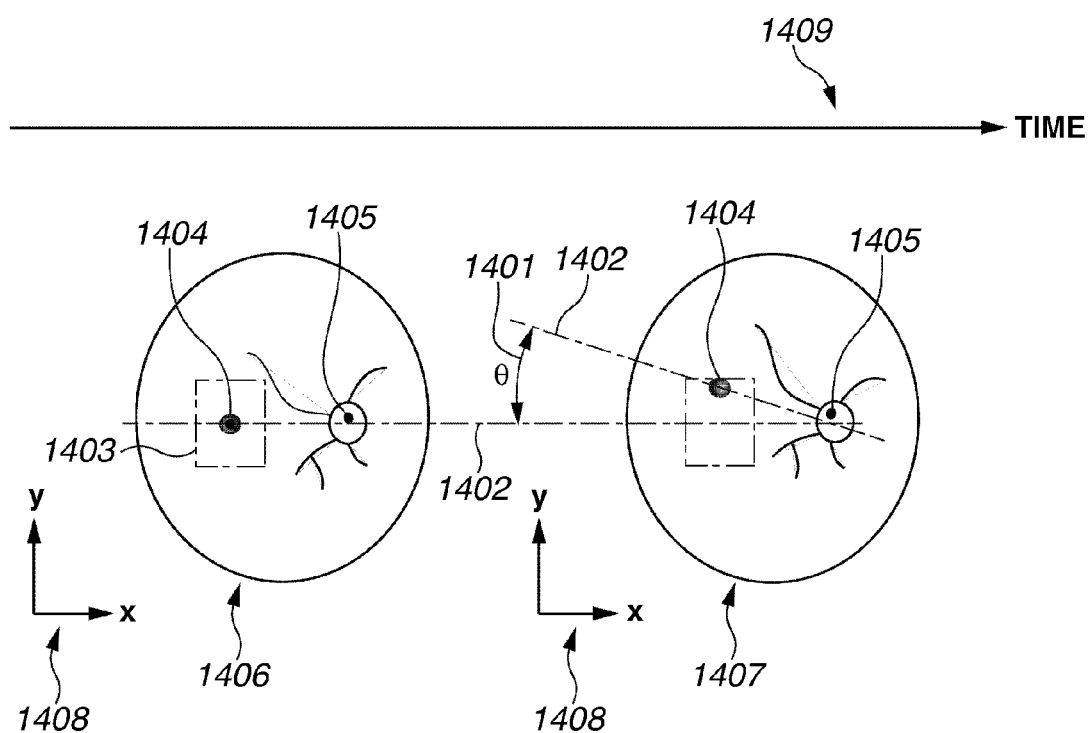
FIG. 14 illustrates the amount of rotation of the fundus according to a third exemplary embodiment.
Figure 15:
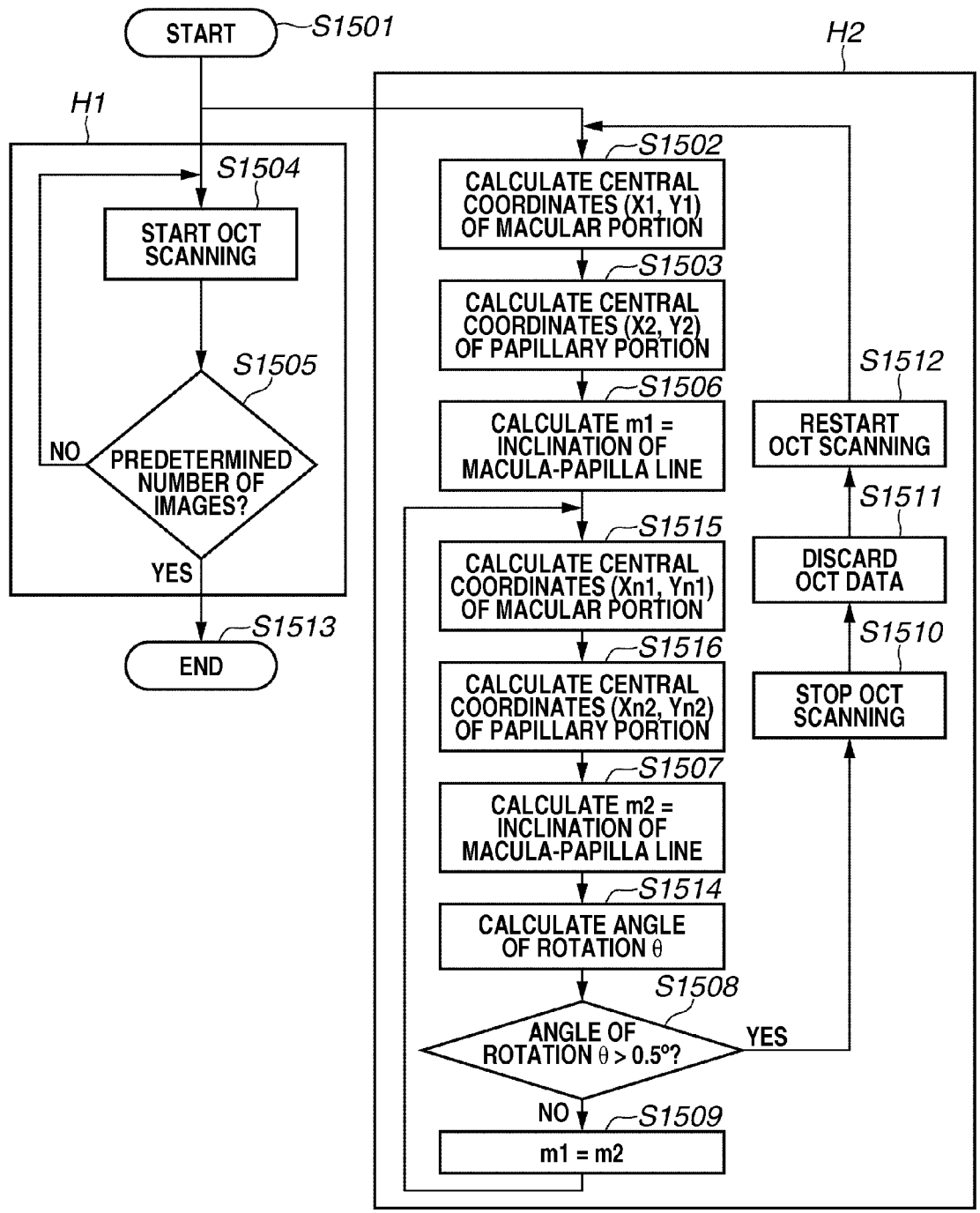
FIG. 15 is a flow chart according to the third exemplary embodiment.

Next, a third exemplary embodiment is described with reference to FIGS. 14 and 15. FIG. 14 illustrates the amount of rotation of the fundus according to the present exemplary embodiment. Further, FIG. 15 is a flow chart according to the present exemplary embodiment. In the present exemplary embodiment, it is determined whether the amount of rotation of the fundus exceeds a threshold. By performing this determination with respect to each tomographic image, it is possible to determine the degree of distortion in a tomographic image which corresponds to the rotation of the fundus. Then, in the present exemplary embodiment, a superposition process such as averaging is performed using tomographic images in each of which the amount of rotation of the fundus is determined to be equal to or smaller than the threshold. This enables the acquisition of a tomographic image with reduced distortion. The image processing on the tomographic images may be not only a superposition process but also three-dimensional reconstruction.

In FIG. 14, time progresses to the right along a time axis 1409. The SLO has an absolute coordinate system 1408 where the vertical axis is a y-axis, and the horizontal axis is an x-axis. FIG. 14 illustrates a scanning area 1403 of OCT. A fundus image 1406 is obtained at the start of OCT scanning. A fundus image 1407 is obtained when n microseconds has elapsed since the start of the OCT scanning. Each of the fundus images 1406 and 1407 includes a macular portion 1404 and a papillary portion 1405. A line 1402 passes through the centers of the macular portion 1404 and the papillary portion 1405. The centers of the macular portion 1404 and the papillary portion 1405 are calculated by image processing. An angle 1401 is formed by the line 1402 at the start of the OCT scanning and the line 1402 of the fundus image during the OCT scanning. Hereinafter, the angle 1401 is represented as an angle of rotation θ1401. The angle of rotation θ1401 is calculated as follows. The central coordinates of the macular portion 1404 at the start of the OCT scanning are represented as $(X_1, Y_1)$, and the central coordinates of the papillary portion 1405 at the start of the OCT scanning are represented as $(X_2, Y_2)$. The central coordinates of the macular portion 1404 during the OCT scanning are represented as $(X_{n1}, Y_{n1})$, and the central coordinates of the papillary portion 1405 during the OCT scanning are represented as $(X_{n2}, Y_{n2})$. An inclination $m_1$ of the line 1402 at the start of the OCT scanning is calculated as follows.

$$m_1 = (Y_2 - Y_1)/(X_2 - X_1)$$

An inclination $m_2$ of the line 1402 during the OCT scanning is calculated as follows.

$$m_2 = (Y_{n2} - Y_{n1})/(X_{n2} - X_{n1})$$

The angle of rotation θ1401 between the line 1402 at the start of the OCT scanning and the line 1402 obtained n microseconds later during the OCT scanning are calculated as follows.

$$\theta = \tan^{-1}\left(\frac{m_2 - m_1}{1 + m_2 m_1}\right) \quad \text{Formula 2}$$

As described above, the angle of rotation θ1401 is calculated every time the SLO performs scanning. Thus, the amount of shift of the fundus in the rotational direction is calculated.

(Flow of Determining Whether Amount of Rotation of Fundus Exceeds Threshold)

Next, the flow of determining whether the amount of rotation (the angle of rotation) of the fundus exceeds a threshold, is described below with reference to FIG. 15. First, in step S1501, the control unit 300 starts the flow. After step S1501, blocks H1 and H2 are processed in parallel.

First, the flow in the parallel processing block H1 is described. In step S1504, the control unit 300 starts OCT scanning. In step S1505, the control unit 300, which is an example of a determination unit, determines whether tomographic image data (OCT data) having a predetermined number of images has been acquired by the OCT scanning. If tomographic image data having the predetermined number of images has not been acquired (NO in step S1505), the processing returns to step S1504. If tomographic image data having the predetermined number of images has been acquired (YES in step S1505), the processing proceeds to step S1513, and the entire processing is ended.

Next, the flow in the parallel processing block H2 is described. In step S1502, the control unit 300, which is an example of a calculation unit, calculates the central coordinates $(X_1, Y_1)$ of the macular portion. In step S1503, the control unit 300, which is an example of the calculation unit, calculates the central coordinates $(X_2, Y_2)$ of the papillary portion. In step S1506, the control unit 300 calculates the inclination of the macula-papilla center line and substitutes the calculated inclination for $m_1$. In step S1515, the control unit 300 calculates the central coordinates $(X_{n1}, Y_{n1})$ of the macular portion obtained n microseconds later. In step S1516, the control unit 300 calculates the central coordinates $(X_{n2}, Y_{n2})$ of the papillary portion obtained n microseconds later. In step S1507, the control unit 300 calculates the inclination of the macula-papilla center line obtained n microseconds later, and substitutes the calculated inclination for $m_2$. In step S1514, the control unit 300 calculates the angle of rotation θ. In step S1508, the control unit 300, which is an example of the determination unit, determines whether the angle of rotation θ exceeds 0.5° (degrees). If it is determined that the angle of rotation θ is equal to or smaller than 0.5° (NO in step S1508), the processing proceeds to step S1509. In step S1509, the control unit 300 substitutes the inclination $m_2$ calculated in step S1507 for $m_1$, and the processing returns to step S1515. If it is determined that the angle of rotation θ exceeds 0.5° (YES step S1508), the processing proceeds to step S1510. In step S1510, the control unit 300 stops the OCT scanning. In step S1511, the control unit 300 discards (deletes) tomographic image data (OCT data) from a memory (not illustrated). In step S1512, the control unit 300 restarts the OCT scanning, and the processing returns to step S1502. After the parallel processing block H1, then in step S1513, the control unit 300 ends the flow and also stops the flow in the parallel processing block H2.

As described above, in the present exemplary embodiment, if it is determined that the angle of rotation θ exceeds 0.5°, the control unit 300 suspends the OCT scanning and discards tomographic image data from the memory (not illustrated). Further, if it is determined that the angle of rotation θ is equal to or smaller than 0.5°, the control unit 300 stores tomographic image data in the memory (not illustrated). At that time, the control unit 300, which is an example of an image processing unit, performs a superposition process such as averaging using the stored tomographic image data, and thereby can acquire a tomographic image with reduced distortion.

In the present exemplary embodiment, the threshold for the amount of rotation is 0.5°, but may be any value so long as distortion in a tomographic image can be reduced based on the value. Further, the present exemplary embodiment assumes the determination during the OCT scanning. Alternatively, after the OCT scanning has ended, the control unit 300, which is an example of the determination unit, may determine whether the amount of rotation (the angle of rotation) of the fundus exceeds the threshold with respect to each piece of image data obtained by the OCT scanning. In this case, the step of suspending the OCT scanning and the step of restarting the OCT scanning can be omitted. Further, according to the above determination, the control unit 300, which is an example of a display control unit, may cause a display unit to display a display form indicating the degree of distortion in a tomographic image which corresponds to the rotation of the fundus, in such a manner that the display form is associated with the tomographic image.

<Determine Whether Amount of Movement in X and Y Directions Exceeds Threshold>

Figure 16:
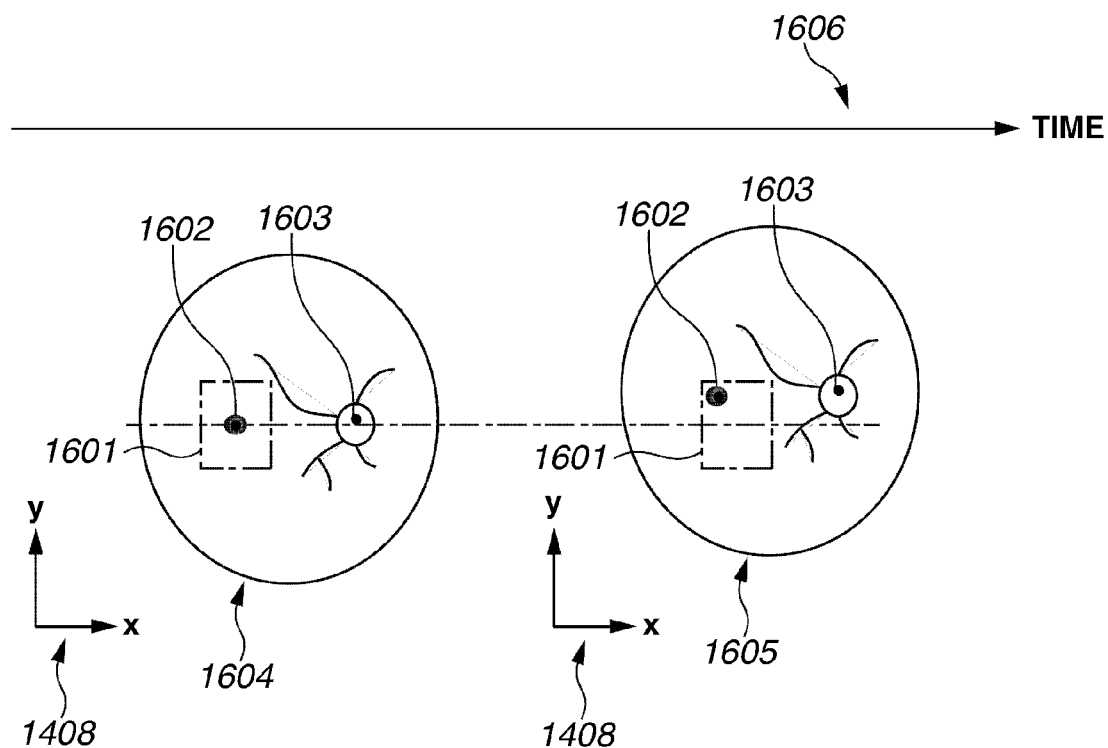
FIG. 16 illustrates the amount of rotation of the fundus according to a fourth exemplary embodiment.
Figure 17:
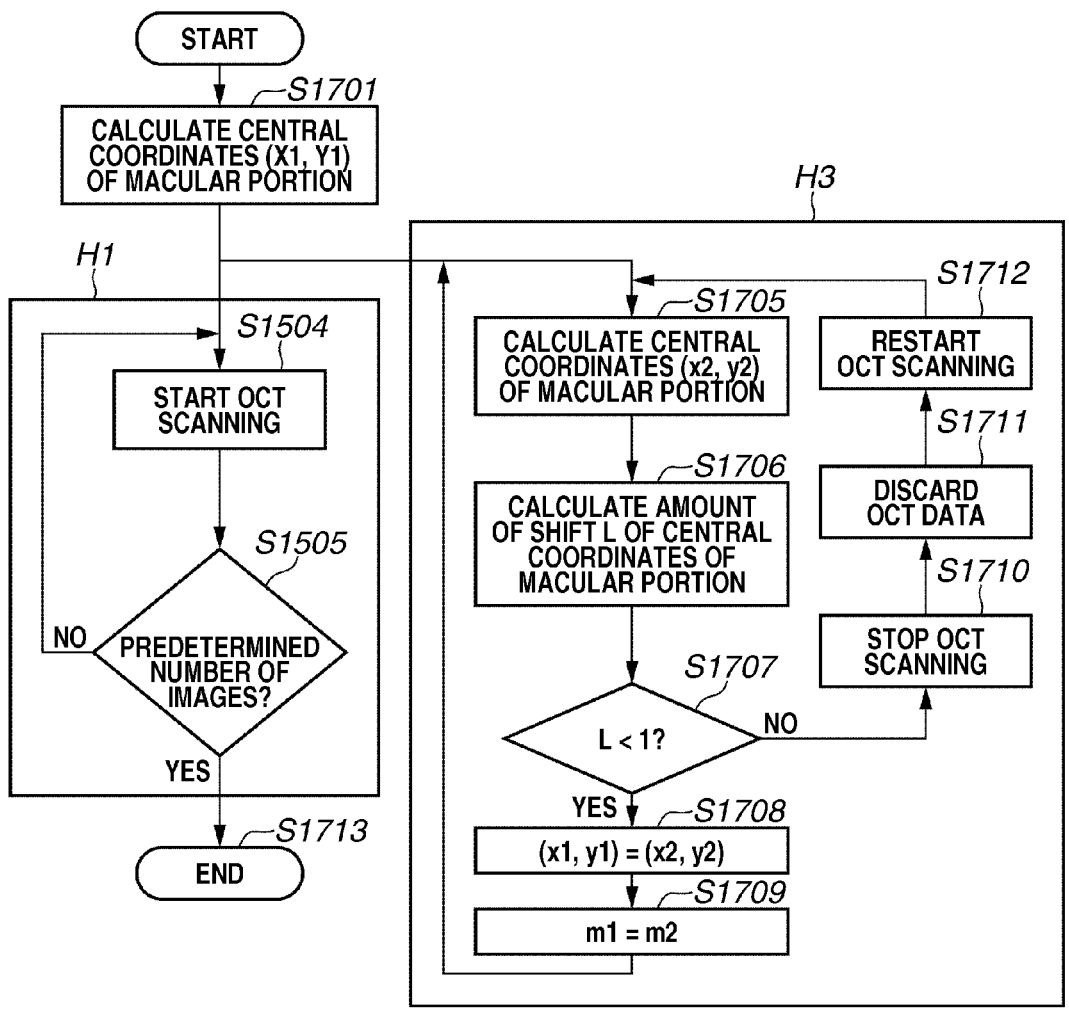
FIG. 17 is a flow chart according to the fourth exemplary embodiment.

Next, a fourth exemplary embodiment is described with reference to FIGS. 16 and 17. FIG. 16 illustrates the amount of movement of the fundus in the X and Y directions in the present exemplary embodiment. Further, FIG. 17 is a flow chart according to the present exemplary embodiment. In the present exemplary embodiment, it is determined whether the amount of movement of the fundus in the X and Y directions exceeds a threshold. By performing this determination with respect to each tomographic image, it is possible to determine the degree of distortion in a tomographic image which corresponds to the movement of the fundus in the X and Y directions. Then, in the present exemplary embodiment, a superposition process such as averaging is performed using tomographic images in each of which the amount of movement of the fundus in the X and Y directions is equal to or smaller than the threshold based on the determination. This enables the acquisition of a tomographic image with reduced distortion. The image processing on the tomographic images may be not only a superposition process but also three-dimensional reconstruction.

In FIG. 16, time progresses to the right along a time axis 1606. The SLO has an absolute coordinate system 1408 where the vertical axis is a y-axis, and the horizontal axis is an x-axis. FIG. 16 illustrates a scanning area 1601 of OCT. A fundus image 1604 is obtained at the start of OCT scanning. A fundus image 1605 is obtained when n microseconds has elapsed since the start of the OCT scanning. Each of the fundus images 1604 and 1605 includes a macular portion 1602 and a papillary portion 1603. The amount of movement of the fundus is calculated as follows. The central coordinates of the macular portion 1602 at the start of the OCT scanning are represented as $(X_1, Y_1)$, and the central coordinates of the macular portion 1602 when n microseconds has elapsed since the start of the OCT scanning are represented as $(X_{n1}, Y_{n1})$. An amount of movement L at this time is calculated as follows.

$$L = \{(X_1 - X_{n1})^2 + (Y_1 - Y_{n1})^2\}^{\frac{1}{2}} \quad \text{Formula 3}$$

As described above, the amount of movement L is calculated every time the SLO performs scanning. Thus, the amount of movement of the fundus in the X and Y directions is calculated.

<Flow of Determining Whether Amount of Movement of Fundus in X and Y Directions Exceeds Threshold>

Next, referring to FIG. 17, a flow of determining whether an amount of movement of the fundus in the X and Y directions exceeds a threshold, is described. First, in step S1701, the control unit 300 starts the flow. After step S1701, blocks H1 and H3 are processed in parallel. The parallel processing block H1 is similar to that in FIG. 15.

Next, the flow in the parallel processing block H3 is described. In step S1705, the control unit 300, which is an example of a calculation unit, calculates the central coordinates $(x_2, y_2)$ of the macular portion obtained n microseconds later. In step S1706, the control unit 300, which is an example of the calculation unit, calculates the amount of shift L of the central coordinates of the macular portion. In step S1707, the control unit 300, which is an example of the determination unit, determines whether the amount of shift L is smaller than 1 pixel. If it is determined that the amount of shift L is smaller than 1 pixel (YES in step S1707), the processing proceeds to step S1708. In step S1708, the control unit 300 substitutes $(x_2, y_2)$ for $(x_1, y_1)$, and the processing returns to step S1705. If it is determined that the amount of shift L is equal to or larger than 1 pixel (NO in step S1707), the processing proceeds to step S1710. In step S1710, the control unit 300 stops the OCT scanning. In step S1711, the control unit 300 discards (deletes) tomographic image data (OCT data) from a memory (not illustrated). In step S1712, the control unit 300 restarts the OCT scanning, and the processing returns to step S1705.

In the present exemplary embodiment, if it is determined that the amount of movement L in the X and Y directions is equal to or larger than 1 pixel, the control unit 300 suspends the OCT scanning and discards tomographic image data from the memory (not illustrated). Further, if it is determined that the amount of movement L in the X and Y directions is smaller than 1 pixel, the control unit 300 stores tomographic image data in the memory (not illustrated). At that time, the control unit 300, which is an example of an image processing unit, performs a superposition process such as averaging using the stored tomographic image data, and thereby can acquire a tomographic image with reduced distortion.

In the present exemplary embodiment, the threshold for the amount of movement in the X and Y directions is 1 pixel, but may be any value so long as distortion in a tomographic image can be reduced based on the value. Further, the present exemplary embodiment assumes the determination during the OCT scanning. Alternatively, after the OCT scanning has ended, the control unit 300, which is an example of the determination unit, may determine whether the amount of movement of the fundus in the X and Y directions exceeds the threshold with respect to each piece of image data obtained by the OCT scanning. In this case, the step of suspending the OCT scanning and the step of restarting the OCT scanning can be omitted. Further, according to the above determination, the control unit 300, which is an example of a display control unit, may cause a display unit to display a display form indicating the degree of distortion in a tomographic image which corresponds to the movement of the fundus in the X and Y directions, in such a manner that the display form is associated with the tomographic image.

Further, in the present exemplary embodiment, the amount of movement L is calculated using the central coordinates of the macular portion 1602 as a region of interest. Alternatively, the amount of movement L may be calculated using the central coordinates of the papillary portion 1603 as a region of interest. As a matter of course, the amount of movement in the X and Y directions in the present exemplary embodiment and the amount of rotation of the fundus in the third exemplary embodiment may be taken into account together. Alternatively, not only the amount of movement in the X and Y directions but also the amount of movement in the Z-direction may be calculated. Further, if each of these amounts of movement exceeds a threshold, notification information such as an alarm message may be output. The notification information may be visual information such as a message displayed on the display unit, or auditory information such as an alarm sound, or any other perceptual information.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-017660 filed Jan. 31, 2013, which is hereby incorporated by reference herein in its entirety.

What is claimed is:

1. An optical coherence tomographic imaging apparatus comprising:
   an image acquisition unit configured to acquire a plurality of images of a subject's eye at different times;
   a tomographic image acquisition unit configured to acquire a plurality of tomographic images of the subject's eye using interference light obtained by causing light reflected from the subject's eye irradiated with measurement light through a scanning unit which scans the subject's eye at repeated intervals, to interfere with reference light corresponding to the measurement light;
   a movement amount acquisition unit configured to acquire an amount of rotation of the subject's eye using the plurality of images; and
   a control unit configured to control the scanning unit to perform, using the acquired amount of rotation, scanning position correction in at least one interval between the end of one scan by the scanning unit and the start of a next scan by the scanning unit.

2. The optical coherence tomographic imaging apparatus according to claim 1, further comprising:
   a determination unit configured to determine whether the acquired amount of rotation exceeds a threshold; and
   a display control unit configured to cause, in a case the determination unit determines that the amount of rotation exceeds the threshold, a display unit to display an alarm message.

3. The optical coherence tomographic imaging apparatus according to 1, further comprising:
   a determination unit configured to determine whether the amount of rotation exceeds a threshold; and
   a display control unit configured to cause, in a case the determination unit determines that the amount of rotation exceeds the threshold, a display unit to display a display form indicating a degree of distortion in a tomographic image of the subject's eye.

4. The optical coherence tomographic imaging apparatus according to claim 1, further comprising:
   a determination unit configured to determine whether the amount of rotation exceeds a threshold; and
   an image processing unit configured to perform image processing on any of the plurality of tomographic images in each of which the acquired amount of rotation is equal to or smaller than the threshold.

5. The optical coherence tomographic imaging apparatus according to claim 4, wherein the image processing unit performs a superposition process on the tomographic images in each of which the acquired amount of rotation is equal to or smaller than the threshold.

6. The optical coherence tomographic imaging apparatus according to claim 1, further comprising:
   a storage unit configured to store the plurality of tomographic images; and
   a determination unit configured to determine whether the amount of rotation exceeds a threshold,
   wherein the control unit deletes from the storage unit any of the plurality of tomographic images in each of which the acquired amount of rotation exceeds a threshold.

7. The optical coherence tomographic imaging apparatus according to claim 1,
   wherein the image acquisition unit acquires a plurality of fundus images of the subject's eye as the plurality of images,
   wherein the movement amount acquisition unit acquires an amount of rotation of the subject's eye and an amount of movement of the subject's eye in X and Y directions using the plurality of fundus images, and
   wherein the control unit controls the scanning unit to perform, using the acquired amount of rotation and the acquired amount of movement in the X and Y directions, the scanning position correction in at least one interval between the end of the one scan and the start of the next scan.

8. The optical coherence tomographic imaging apparatus according to claim 1, wherein the control unit controls the scanning unit to correct the scanning position between a main scan and a next main scan performed by the scanning unit, and to stop correcting the scanning position while the scanning unit is performing main scanning.

9. The optical coherence tomographic imaging apparatus according to claim 1, wherein the control unit controls the scanning unit to correct the scanning position while the scanning unit is performing sub-scanning, and to stop correcting the scanning position while the scanning unit is performing main scanning.

10. An optical coherence tomographic imaging apparatus comprising:
    an image acquisition unit configured to acquire a plurality of images of a subject's eye at different times;
    a tomographic image acquisition unit configured to acquire a plurality of tomographic images of the subject's eye using interference light obtained by causing light reflected from the subject's eye irradiated with measurement light through a scanning unit which scans the subject's eye at repeated intervals, to interfere with reference light corresponding to the measurement light;
    a movement amount acquisition unit configured to acquire an amount of movement of the subject's eye using the plurality of images;
    a control unit configured to control the scanning unit to perform, using the acquired amount of movement, scanning position correction in at least one interval between the end of one scan by the scanning unit and the start of a next scan performed by the scanning unit; and
    an image processing unit configured to perform image processing on any of the plurality of tomographic images in each of which the acquired amount of movement is equal to or smaller than a threshold.

11. A method of controlling an optical coherence tomographic imaging apparatus for acquiring a plurality of tomographic images of a subject's eye using interference light obtained by causing light reflected from the subject's eye irradiated with measurement light through a scanning unit which scans the subject's eye at repeated intervals, to interfere with reference light corresponding to the measurement light, the method comprising:
    acquiring an amount of rotation of the subject's eye using a plurality of images of the subject's eye acquired at different times; and
    controlling the scanning unit to perform, using the acquired amount of rotation, scanning position correction in at least one interval between the end of one scan by the scanning unit and the start of a next scan by the scanning unit.

12. The method of controlling the optical coherence tomographic imaging apparatus according to claim 11, further comprising:
    determining whether the acquired amount of rotation exceeds a threshold; and
    causing, in a case it is determined that the amount of rotation exceeds the threshold, a display unit to display an alarm message.

13. The method of controlling the optical coherence tomographic imaging apparatus according to claim 11, further comprising:
    determining whether the amount of rotation exceeds a threshold; and
    causing, in a case it is determined that the amount of rotation exceeds the threshold, a display unit to display a display form indicating a degree of distortion in a tomographic image of the subject's eye.

14. The method of controlling the optical coherence tomographic imaging apparatus according to claim 11, further comprising:
    determining whether the amount of rotation exceeds a threshold; and
    performing image processing on any of the plurality of tomographic images in each of which the acquired amount of rotation is equal to or smaller than the threshold.

15. The method of controlling the optical coherence tomographic imaging apparatus according to claim 14, wherein in the image processing, a superposition process is performed on the tomographic images in each of which the acquired amount of rotation is equal to or smaller than the threshold.

16. The method of controlling the optical coherence tomographic imaging apparatus according to claim 11, further comprising:
- storing in a storage unit the plurality of tomographic images;
- determining whether the amount of rotation exceeds a threshold; and
- deleting from the storage unit any of the plurality of tomographic images in each of which the acquired amount of rotation exceeds the threshold.

17. The method of controlling the optical coherence tomographic imaging apparatus according to claim 11, wherein the plurality of images are a plurality of fundus images of the subject's eye,
- wherein, in the acquisition of the amount of movement, an amount of rotation of the subject's eye and an amount of movement of the subject's eye in X and Y directions are acquired using the plurality of fundus images, and
- wherein in the controlling, the scanning unit is controlled to perform, using the acquired amount of rotation and the acquired amount of movement in the X and Y directions, the scanning position correction in at least one interval between the end of the one scan and the start of the next scan.

18. A non-transitory computer-readable storage medium storing a program for causing a computer to execute the method of controlling the optical coherence tomographic imaging apparatus according to claim 11.

19. A method of controlling an optical coherence tomographic imaging apparatus for acquiring a plurality of tomographic images of a subject's eye using interference light obtained by causing light reflected from the subject's eye irradiated with measurement light through a scanning unit which scans the subject's eye at repeated intervals, to interfere with reference light corresponding to the measurement light, the method comprising:
- acquiring an amount of movement of the subject's eye using a plurality of images of the subject's eye acquired at different times;
- controlling the scanning unit to perform, using the acquired amount of movement, scanning position correction in at least one interval between the end of one scan by the scanning unit and the start of a next scan by the scanning unit; and
- performing image processing on any of the plurality of tomographic images in each of which the acquired amount of movement is equal to or smaller than a threshold.

20. A non-transitory computer-readable storage medium storing a program for causing a computer to execute the method of controlling the optical coherence tomographic imaging apparatus according to claim 19.

* * * * *